(12) United States Patent
Fukushima et al.

(10) Patent No.: US 9,109,867 B2
(45) Date of Patent: Aug. 18, 2015

(54) WELD DETECTING METHOD AND WELD DETECTING APPARATUS

(75) Inventors: Masato Fukushima, Toyota (JP); Yuji Suzuki, Kariya (JP); Shinichi Iwazaki, Toyota (JP)

(73) Assignee: TOYOTA JIDOSHA KABUSHIKI KAISHA, Toyota-Shi (JP)

( * ) Notice: Subject to any disclaimer, the term of this patent is extended or adjusted under 35 U.S.C. 154(b) by 732 days.

(21) Appl. No.: 13/509,847

(22) PCT Filed: Nov. 16, 2010

(86) PCT No.: PCT/IB2010/003111
§ 371 (c)(1),
(2), (4) Date: May 15, 2012

(87) PCT Pub. No.: WO2011/058444
PCT Pub. Date: May 19, 2011

(65) Prior Publication Data
US 2012/0232822 A1    Sep. 13, 2012

(30) Foreign Application Priority Data

Nov. 16, 2009  (JP) ................................. 2009-261159

(51) Int. Cl.
| | |
|---|---|
| *G01B 5/04* | (2006.01) |
| *G01B 11/04* | (2006.01) |
| *G01B 7/04* | (2006.01) |
| *G01B 5/00* | (2006.01) |
| *G01N 19/08* | (2006.01) |

(52) U.S. Cl.
CPC ............ *G01B 5/0037* (2013.01); *G01B 11/046* (2013.01); *G01N 19/08* (2013.01)

(58) Field of Classification Search
CPC ..... G01B 5/0037; G01B 11/046; G01B 11/02; G01B 11/06; G01B 11/0691; G01B 7/10; G01B 7/06; G01B 7/07; G01B 7/02; G01N 19/08; G01N 27/82
See application file for complete search history.

(56) References Cited

U.S. PATENT DOCUMENTS 5,493,221 A    2/1996  Wertz

FOREIGN PATENT DOCUMENTS

| JP | 60249004 A | * 12/1985 | ............. G01B 11/00 |
|---|---|---|---|
| JP | 61-151455 A | 7/1986 | |
| JP | 03-047625 A | 2/1991 | |

(Continued)

OTHER PUBLICATIONS

International Search Report and Written Opinion of PCT/IB2010/003111 mailed Apr. 14, 2011.

*Primary Examiner* — Manuel L Barbee
(74) *Attorney, Agent, or Firm* — Kenyon & Kenyon LLP

(57) ABSTRACT

A weld detecting method that detects a weld on a work includes: obtaining in advance at least one correlation, from among a correlation between a width of the neck and an amount of elongation of the work and a correlation between the width of the neck and an amount of change in at least one of a sheet thickness and a sheet width of the work before and after elongation of the work, and calculating the width of the neck based on the at least one correlation by obtaining at least one of the sheet thickness, the sheet width, or the amount of elongation of the work from the obtained at least one correlation; setting a conveying speed, according to the calculated width of the neck; and detecting the neck by measuring the sheet width of the work at predetermined intervals, while conveying the work the set conveying speed.

6 Claims, 17 Drawing Sheets

(56) References Cited

FOREIGN PATENT DOCUMENTS

| JP | 2001-153645 A | 6/2001 |
| JP | 2005-283303 A | 10/2005 |
| JP | 2006-132942 A | 5/2006 |
| JP | 2006-183078 A | 7/2006 |

* cited by examiner

WELD DETECTING METHOD AND WELD DETECTING APPARATUS

This is a 371 national phase application of PCT/IB2010/003111 filed 16Nov. 2010, claiming priority to Japanese Patent Application No. 2009-261159 filed 16 Nov. 2009, the contents of which are incorporated herein by reference.

BACKGROUND OF THE INVENTION

1. Field of the Invention

The invention relates to a weld detecting method and a weld detecting apparatus that detect a position of a weld on a work.

2. Description of the Related Art

When forming a work by joining two end portions of sheet-like portions together by welding, for example, a weld is formed on the work. In the work, the characteristics such as hardness and the like of the weld are different than they are at other portions. Therefore, it is necessary to detect the position of a weld in order to check just the weld or perform machining on portions other than the weld. However, when a worker detects, through visual confirmation, a weld on a work that has been elongated by rolling or the like, it is extremely difficult to discern the position of the weld, so detection takes more time. Examples of such a work include metal rings and metal bands.

Japanese Patent Application Publication No. 61-151455 (JP-A-61-151455) and Japanese Patent Application Publication No. 2005-283303 (JP-A-2005-283303), for example, describe weld detecting methods.

JP-A-61-151455 describes detecting a weld on a work after rolling. In JP-A-61-151455, a movable detection sensor is used to detect a weld on a work after rolling. The detection sensor generates an eddy current inside the work and detects a weld by detecting this eddy current with a detecting portion. Also, a detection signal detected by the detecting portion is filtered by a filtering portion. This kind of detection sensor is moved around to detect the weld. Accordingly, noise included in the detection signal can be removed by the filtering portion so a weld on a work after rolling can be detected.

The technology in JP-A-61-151455 detects a weld by detecting a change in impedance from the eddy current. Therefore, when detecting a weld on a work that has been heat-treated, the crystal composition of the work has been made uniform, so the weld may be undetectable. That is, the detection accuracy may be reduced.

Also, JP-A-2005-283303 describes technology for detecting a flaw in a metal ring. In the technology described in JP-A-2005-283303, a driving pulley, a driven pulley, and a benchmark index detecting mechanism are used to detect a flaw in a metal ring. The metal ring is wound around the driving pulley and the driven pulley. The benchmark index detecting mechanism is arranged between the driving pulley and the driven pulley, and image-verifies a weld trace formed along the sheet width of the metal ring at the weld. The driving pulley is rotated to convey the work, and the position of the weld trace is detected by the benchmark index detecting mechanism. Also, flaw detection is performed by a mechanism that detects a flaw in a metal ring, and the detected position is identified as a relative position from the weld trace. The weld on the work is able to be detected using this kind of benchmark index detecting mechanism that detects a weld trace.

However, when a weld on a work is detected using the technology described in JP-A-2005-283303, the coloring and shape of the weld trace may change depending on the welding conditions such as the bead width and the like. That is, the weld trace may become difficult to see and thus may not be able to be detected. As a result, the accuracy with which a weld is detected may decrease. Also, although it is possible to reduce the rotation speed of the driving pulley to increase the detection accuracy, doing so would increase the time that it takes to detect the weld.

Also, a neck (an extremely small change) like a cutout toward the inside in the sheet width direction is formed at a weld on a work that has been rolled after welding. While it is possible to detect a weld on a work by detecting this kind of neck, the conveying speed of the work must be increased in order to detect the neck quickly, which means that an expensive sensor with extremely short measurement intervals must be used. That is, it is costly. On the other hand, if a sensor with long measurement intervals is used, the speed at which the neck is conveyed must be slowed so as to not skip over the neck. That is, it takes more time to detect the weld.

SUMMARY OF INVENTION

The invention provides a weld detecting method and a weld detecting apparatus capable of both reducing the time that it takes to detect a weld on a work and detecting a weld at low cost.

A first aspect of the invention relates to a weld detecting method that detects a weld on a work having a weld, by detecting a neck formed at the weld on the work, when elongating the work. This weld detecting method includes obtaining at least one correlation, from among a correlation between a width of the neck and an amount of elongation of the work and a correlation between the width of the neck and an amount of change in at least one of a sheet thickness and a sheet width of the work before and after elongation of the work, and calculating the width of the neck based on the at least one correlation by obtaining at least one of the sheet thickness, the sheet width, and the amount of elongation of the work from the obtained at least one correlation; setting a conveying speed of the work when detecting the neck, according to the calculated width of the neck; and detecting the neck by measuring the sheet width of the work at predetermined intervals, while conveying the work at the set conveying speed of the work.

The weld detecting method described above may also include resetting at least one of the measurement intervals of the sheet width of the work or the conveying speed of the work when detecting the neck, when the neck is not detected. Also, detection of the neck may be performed by measuring the sheet thickness of the work at the reset conveying speed and/or the reset measurement intervals.

A second aspect of the invention relates to a weld detecting method that detects a weld on a work having a weld, by detecting a neck formed at the weld on the work, while conveying the work at a predetermined conveying speed, when elongating the work. This weld detecting method includes calculating a potential position of the neck by measuring a sheet width of the work, while conveying the work at a speed faster than the predetermined conveying speed; and detecting the neck by measuring the sheet width of the work at the calculated potential position, at the predetermined conveying speed.

In the structure described above, the sheet width of the work may be measured using analog output when conveying the work at the speed faster than the predetermined conveying speed, and the sheet width of the work at the potential position may be measured using digital output when measuring the sheet width of the work at the calculated potential position.

A third aspect of the invention relates to a weld detecting apparatus that detects a weld on a work having a weld, by detecting a neck formed at the weld on the work, when elongating the work. This weld detecting apparatus includes a conveying mechanism that conveys the work, a detecting mechanism that detects an amount of elongation, a sheet width, and a sheet thickness of the work, a calculating portion that calculates a width of the neck based on at least one correlation, from among a correlation between the width of the neck and the amount of elongation of the work and a correlation between the width of the neck and an amount of change in at least one of the sheet thickness and the sheet width of the work before and after elongation of the work, and a setting portion that sets a conveying speed of the conveying mechanism according to the calculated width of the neck. The neck is detected by measuring the sheet width of the work at predetermined intervals by the detecting mechanism, while conveying the work at the set conveying speed.

A fourth aspect of the invention relates to a weld detecting apparatus that detects a weld on a work having a weld, by detecting a neck formed at the weld on the work while conveying the work at a predetermined conveying speed, when elongating the work. This weld detecting apparatus includes a conveying mechanism that conveys the work, a detecting mechanism that detects an amount of elongation, a sheet width, and a sheet thickness of the work, and a calculating portion that sets a conveying speed of the conveying mechanism to a speed faster than the predetermined conveying speed, and calculates a potential position of the neck by measuring the sheet width of the work by the detecting mechanism while conveying the work. The neck is detected by measuring the sheet width of the work at the calculated potential position, at the predetermined conveying speed.

The invention makes it possible to reduce the time that it takes to detect a weld on a work, as well as detect a weld at low cost, by being able to optimally set the speed at which a neck formed at a weld is detected, or reduce the area over which detection of the neck is performed, in the detection of a weld on a work.

BRIEF DESCRIPTION OF DRAWINGS

The foregoing and further objects, features and advantages of the invention will become apparent from the following description of example embodiments with reference to the accompanying drawings, wherein like numerals are used to represent like elements and wherein:

FIG. 8D being a view a weld that has been moved to a stopping position by the weld detecting apparatus;

DETAILED DESCRIPTION OF EMBODIMENTS

Hereinafter, a weld detecting apparatus 1, that detects a weld Y using a weld detecting method according to a first example embodiment will be described with reference to the accompanying drawings.

As shown in FIGS. 1 to 10, the weld detecting apparatus 1 detects a weld Y on a work elongated after being welded, by performing rolling and circumferential adjustment and the like after welding. Some examples of such a work 100 are a metal ring in which both ends of a band-shaped metal sheet have been joined together by welding, and a joined metal band in which the end portions of a plurality of band-shaped metal sheets have been joined together by welding.

Incidentally, the structure of the weld detecting apparatus 1 is different when detecting a weld on a work formed in an annular shape, such as a metal ring, for example, than when detecting a weld on a work formed in a band shape, such as a metal band, for example.

Hereinafter, the weld detecting apparatus 1 when detecting a weld Y an a metal ring will be described. First, the work 100 in which the weld Y is to be detected, i.e., the metal ring, will be described. The work 100 is formed by performing predetermined machining on a member that is formed in a sheet shape, as shown in FIG. 10.

Figure 10:
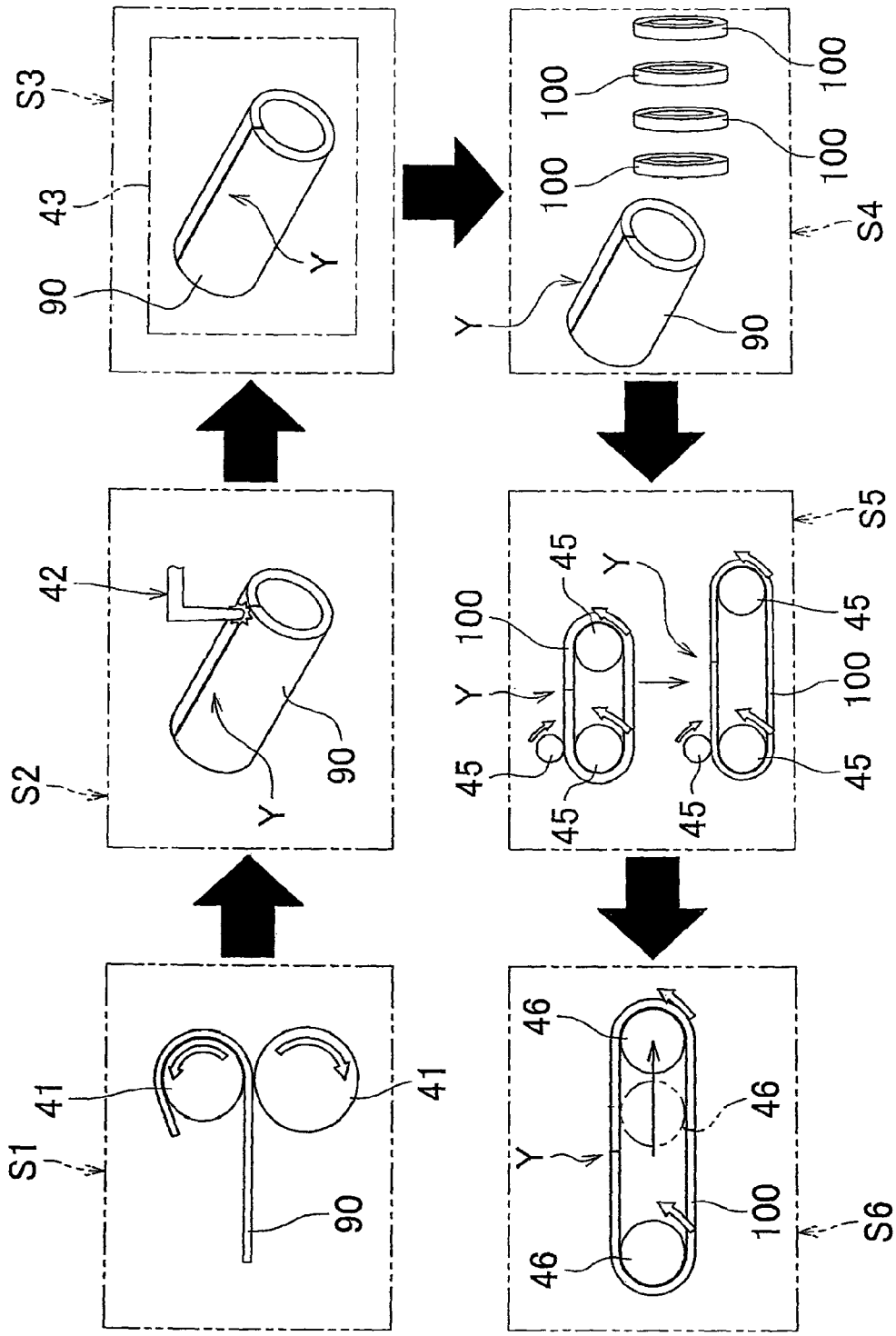
FIG. 10 is a view of the processes involved in forming a metal ring.

As shown in FIG. 10, a metal sheet 90 that is the material for forming the work 100 is bent in a generally cylindrical shape by being squeezed between a pair of bending rollers 41 that rotate, in a bending process S1. At this time, the metal sheet 90 is cut to a length at which both end portions abut against each other.

The metal sheet 90 that has been bent in a cylindrical shape is formed in a generally cylindrical shape by welding both abutting end portions using a predetermined welding mechanism 42 in a welding process S2. As a result, a weld Y is formed on the metal sheet 90.

The welded cylindrical metal sheet 90 is then placed in a heat-treating furnace 43 in a heat-treating process S3.

The heat-treated cylindrical metal sheet 90 is then cut at predetermined intervals by a predetermined cutting mechanism in a cutting process S4. As a result, the cylindrical metal sheet 90 is formed in a ring-shaped work 100.

The work 100 formed by cutting the heat-treated cylindrical metal sheet 90 is then elongated by a plurality of pressure rollers 45 that rotate in a rolling process S5. That is, the work 100 is elongated while being held by the plurality of pressure rollers 45. At this time, the sheet thickness D of the work is reduced (i.e., the sheet becomes thin).

The rolled work 100 is further elongated in a circumferential length adjusting process S6. At this time, the inner peripheral surface of the work 100 is wound around two adjusting rollers 46 that rotate. The work 100 is pulled by moving one of the two adjusting rollers 46 (the adjusting roller 46 on the right side in FIG. 10) outward in the radial direction of the work 100. That is, tension is applied to the work 100 such that the work 100 is elongated.

Here, in the circumferential length adjusting process S6, the work 100 can be elongated with more precision than it can be in the rolling process S5. Therefore, when forming a work 100 with a different circumferential length, the amount of elongation of the work 100 can be changed in the circumferential length adjusting process S6.

Accordingly, the work 100 is formed as a metal ring having a predetermined circumferential length. Also, a plurality of ring-shaped works 100 formed in the cutting process S4 may be formed as a plurality of metal rings having different circumferential lengths. That is, the work 100 may be formed as a plurality of metal rings with different amounts of elongation.

Figure 11:
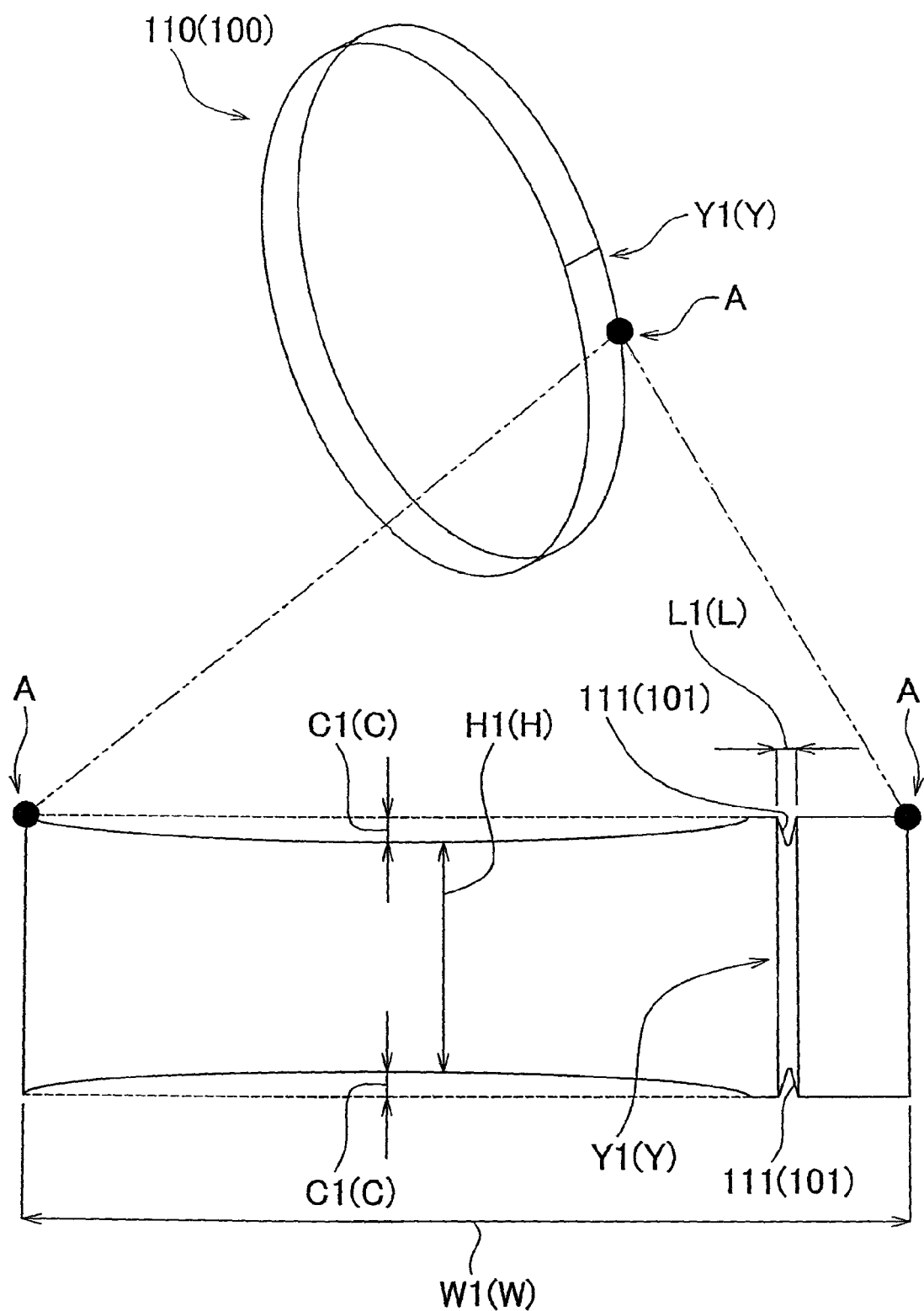
FIG. 11 is a view of a sheet surface of a metal ring when a metal ring with the smallest amount of elongation is cut at point A.
Figure 12:
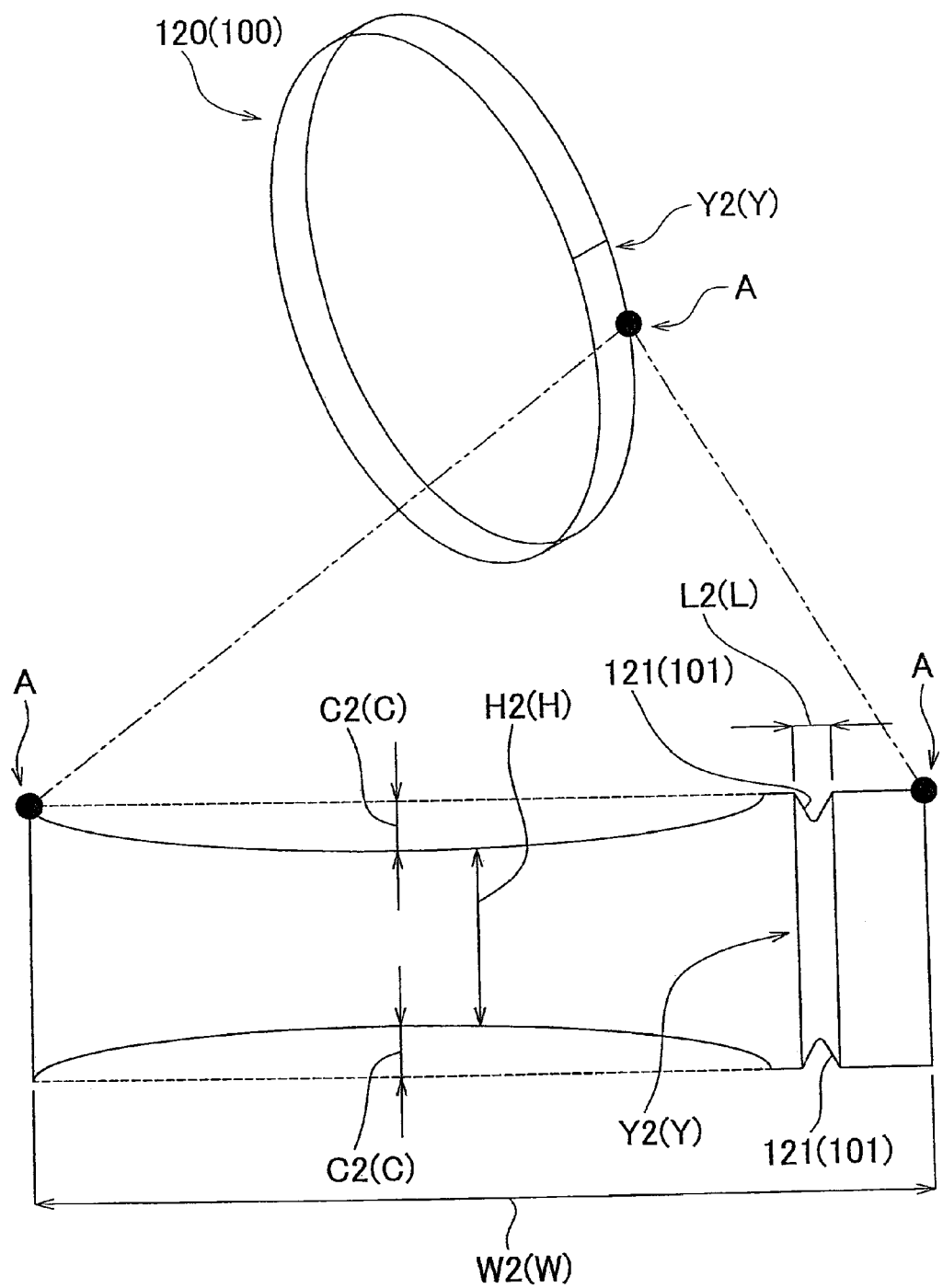
FIG. 12 is a view of a sheet surface of a metal ring when a metal ring with the largest amount of elongation is cut at point A.

Only one weld Y is formed, as shown in FIGS. 11 and 12, on this kind of work 100, and a neck 101 is formed at this weld Y. The neck 101 that is as if the work 100 had been cut away from both end portions toward the inside is formed in the sheet width direction of the work 100. The sheet width H of the portion where the neck 101 is formed is shorter than it is elsewhere. This kind of neck 101 is formed when the work 100 is elongated in the rolling process S5 and the circumferential length adjusting process S6 and the like.

Incidentally, hereinafter, the work with the smallest amount of elongation shown in FIG. 11 will be referred to as "work 110", and the weld thereof will be referred to as "weld Y1". Also, the neck will be referred to as "neck 111". Moreover, the work with the largest amount of elongation shown in FIG. 12 will be referred to as "work 120", and the weld thereof will be referred to as "weld Y2". Also, the neck will be referred to as "neck 121".

Next, the relationship between a change in the sheet width H of the work and the width L of the neck will be described. At the time the cylindrical metal sheet 90 is cut and formed in the cutting process S4, the sheet width H is generally the same over the entire circumference. However, at the time the work 100 is pulled in the circumferential length adjusting process S6, a portion where the sheet width H changes gradually (curves) so as to become smaller (see the dotted line portion shown in FIGS. 11 and 12) is produced in the work 100, as shown in FIGS. 11 and 12. That is, a portion in which the sheet width H is short is formed in the work 100 in the circumferential length adjusting process S6.

A portion H2 where the sheet width of the work 120 with the largest amount of elongation becomes shorter than a portion H1 where the sheet width of the work 110 with the smallest amount of elongation is short. That is, the change in the sheet width H of the work 120 is larger than the change in the sheet width H of the work 110. Here, the work 120 is elongated more than the work 110 in the circumferential length adjusting process S6. That is, the change in the sheet width H increases when pulled more in the circumferential length adjusting process S6.

Incidentally, in the description below, the amount of change in the sheet width H before and after this kind of work 100 undergoes the circumferential length adjusting process S6 (see arrow C1 in FIG. 11 and arrow C2 in FIG. 12) will be referred to as the amount of gradual change C in the sheet width.

Figure 13A:
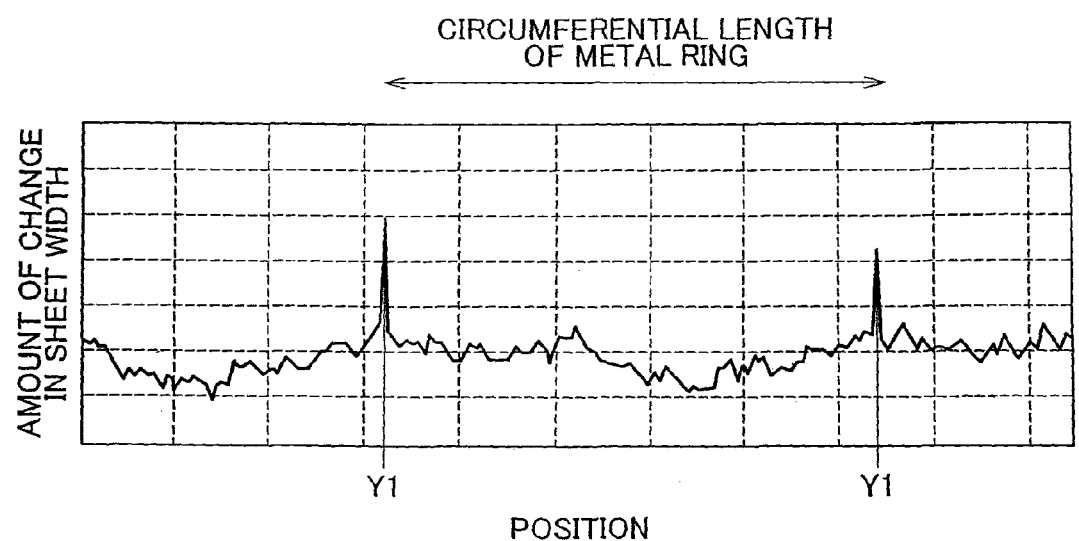
FIGS. 13A and 13B are graphs showing the results from measuring the sheet width of the metal ring, with FIG. 13A being a graph showing the sheet width measurement results for the metal ring with the smallest amount of elongation, and FIG. 13B being a graph showing the sheet width measurement results for the metal ring with the largest amount of elongation.

FIG. 13A shows the results from measuring the sheet width H of the work 110. In this case, it is evident that the amount of change in the sheet width H is large only at the position of the weld Y1 and the amount of change in the sheet width H of the portion other than the weld Y1 is small, due to the effect of the neck 111 formed at the weld Y1. That is, it is evident that the amount of gradual change C1 in the sheet width is small.

Figure 13B:
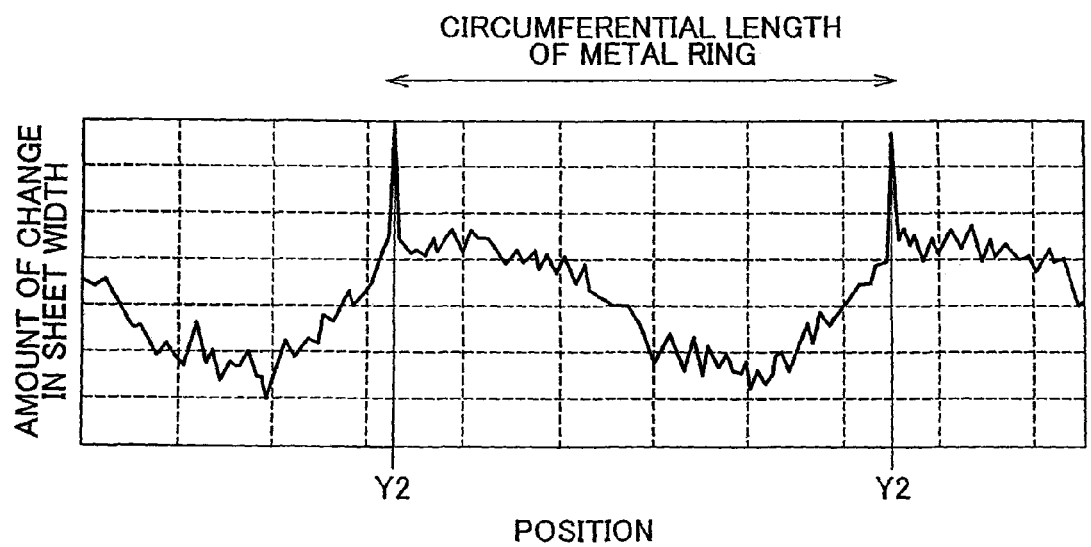

Also, FIG. 13B shows the results from measuring the sheet width H of the work 120. In this case, it is evident that the amount of change in the sheet width H of the overall work is large due to the effect of the neck 121 formed at the weld Y2 and the effect of the gradual change in the sheet width H. That is, it is evident that the amount of gradual change C2 in the sheet width is large.

Figure 14:
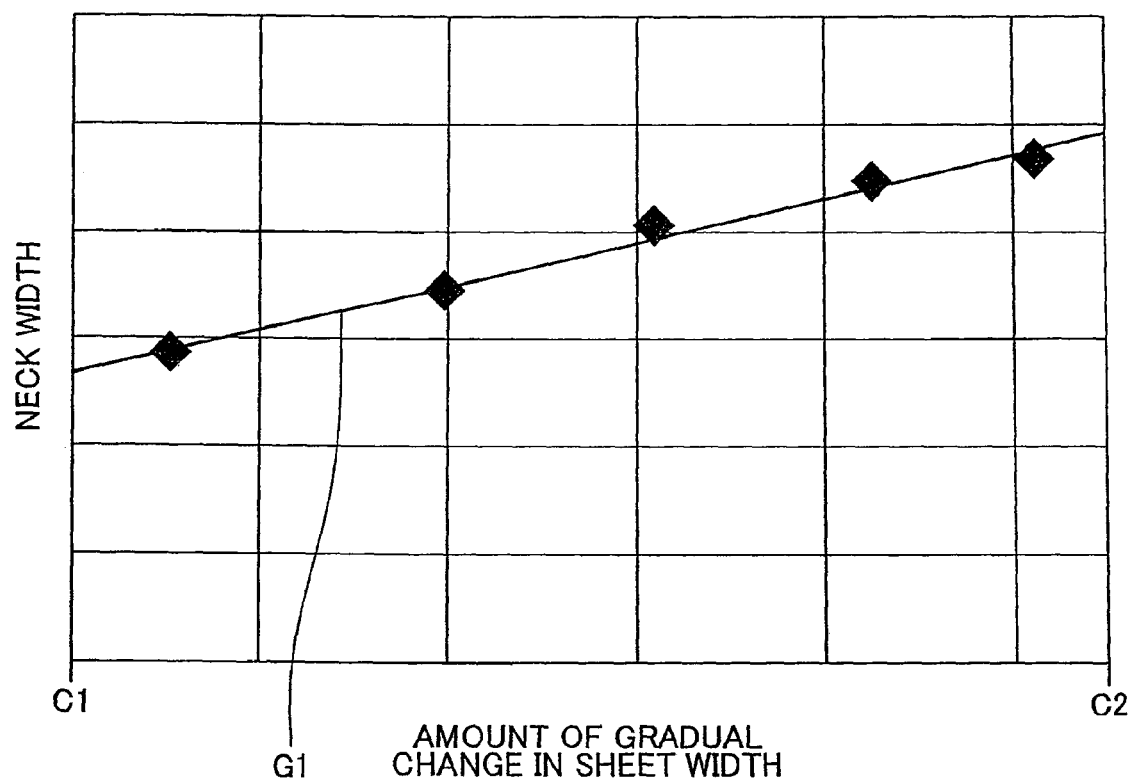
FIG. 14 is a graph showing the correlation between the neck width and the amount of gradual change in the sheet width.

FIG. 14 shows the test results from measuring the width L of the neck corresponding to works 100 having different amounts of gradual change C in the sheet width. As the amount of gradual change C in the sheet width increases, the width L of the neck increases. That is, it is evident that there is a correlation between the amount of gradual change C in the sheet width and the width L of the neck (see graph G1 in FIG. 14). In particular, the width L2 of the neck in the work 120 with the largest amount of gradual change C in the sheet width is approximately twice the length of the width L1 of the neck in the work 110 with the smallest amount of gradual change C in the sheet width.

Figure 1:
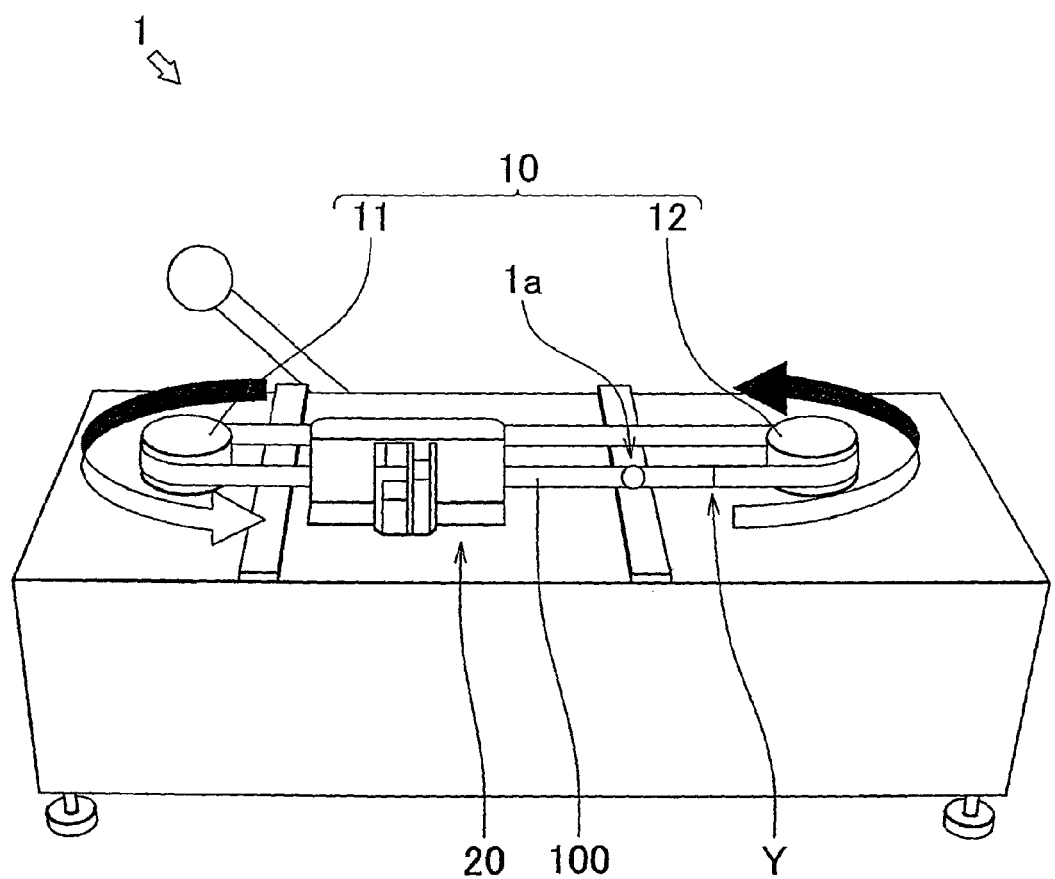
FIG. 1 is a perspective view of the overall structure of a weld detecting apparatus according to a first example embodiment that detects a weld on a metal ring.

Next, the overall structure of the weld detecting apparatus 1 will be described. As shown in FIG. 1, the weld detecting apparatus 1 includes a conveying mechanism 10 and a detecting mechanism 20.

The conveying mechanism 10 conveys the work 100. This conveying mechanism 10 includes a driving pulley 11 and a tension pulley 12. The driving pulley 11 is a member with a generally circular outer shape that is driven by a predetermined driving source. Also, a rotary encoder is mounted on the driving pulley 11. Accordingly, the weld detecting apparatus 1 monitors the rotation of the driving pulley 11. The tension pulley 12 is formed having generally the same shape as the driving pulley 11, and is arranged a predetermined distance away from the driving pulley 11.

The detecting mechanism 20 measures the sheet width H of the work. The detecting mechanism 20 is arranged so as not to interfere with the work 100 when the work 100 is fitted onto the driving pulley 11 and the tension pulley 12. A non-contact laser sensor is used for the detecting mechanism 20 in this example embodiment.

With this kind of weld detecting apparatus 1, the work 100 is fitted onto the conveying mechanism 10 and the driving pulley 11 is rotated. As a result, the tension pulley 12 rotates together with the driving pulley 11, thus conveying the work 100. That is, the work 100 is moved in the circumferential direction with respect to the detecting mechanism 20. At this time, the neck 101 formed at the weld Y is detected by measuring the sheet width H of the work using the detecting mechanism 20. As a result, the weld detecting apparatus 1 detects the weld Y on the work, and conveys the work 100 such that the weld Y is situated at a predetermined position (hereinafter referred to as the "stopping position 1a"). Also, the weld detecting apparatus 1 conveys the work 100 to a predetermined position by rotating the driving pulley 11 a desired number of times.

In the weld detecting apparatus 1, the conveying speed of the work 100 when measuring the sheet width H changes according to the rotation speed of the driving pulley 11. That is, the rotation speed of the driving pulley 11 becomes the conveying speed of the work 100 when measuring the sheet width H. Also, the weld detecting apparatus 1 is configured to be able to set the rotation speed of the driving pulley 11, i.e., to be able to set the conveying speed of the work 100.

Here, when calculating the amount of gradual change C in the sheet width by measuring the sheet width H of the work, it is not necessary to detect the neck 101. Also, the gradual change in the work 100 is large in the circumferential direction of the work 100 (see the dotted line portion in FIG. 11). That is, the gradual change in the work 100 is large in the direction in which the work 100 is pulled. Therefore, even if the neck 101 is skipped over (i.e., even if the sheet width H of the neck 101 portion is unable to be measured), the amount of gradual change C in the sheet width can still be calculated. In the first example embodiment, the conveying speed of the work 100 when measuring the sheet width H of the work in order to calculate the amount of gradual change C in the sheet width, i.e., the speed at which the neck 101 is skipped over (i.e., a speed that is faster than the speed at which the sheet width H of the neck 101 portion can be measured) will be referred to as the "high conveying speed V1".

On the other hand, when detecting the neck 101, it is necessary to increase the resolving power of the detecting mechanism 20 because the width L of the neck is extremely small. Therefore, when the measurement intervals of the detecting mechanism 20 are constant, the conveying speed of the work 100 when measuring the sheet width H must be slower than the high conveying speed V1. In the first example embodiment, the speed when detecting the neck 101, from among the conveying speeds of the work 100 when measuring the sheet width H of the work, will be referred to as the "low conveying speed V2".

The high conveying speed V1 is set to a predetermined speed. Also, the measurement intervals of the sheet width H of the work by the detecting mechanism 20 are set to the shortest measurement intervals, from among the measurement intervals at which the detecting mechanism 20 is capable of taking measurements. The weld detecting apparatus 1 is configured to be able to calculate the width L of the neck based on a correlation between the amount of gradual change C in the sheet width and the width L of the neck that has been obtained beforehand (see graph G1 in FIG. 14). Also, the weld detecting apparatus 1 is configured to be able to set the low conveying speed V2 according to the width L of the neck.

A weld detecting method according to the first example embodiment that is performed using the weld detecting apparatus 1 having the structure described above will now be described.

Figure 2A:
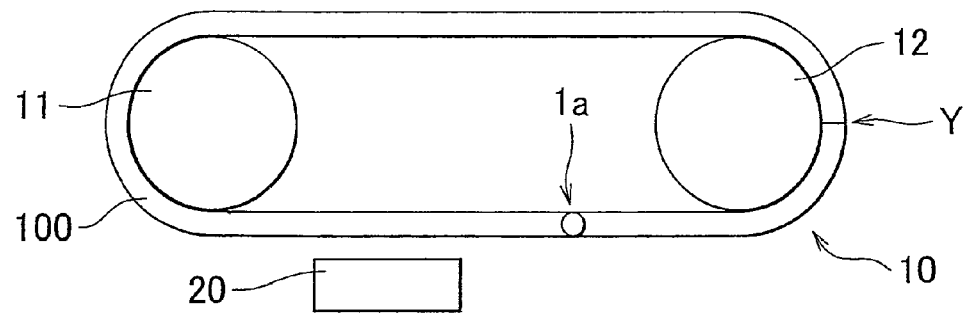
FIGS. 2A to 2D are plan views of the operation of the weld detecting apparatus according to the first example embodiment that detects a weld on a metal ring, with FIG. 2A being a view of a work fitted onto the weld detecting apparatus, FIG. 2B being a view of the weld detecting apparatus measuring the sheet width at high speed, FIG. 2C being a view of the weld detecting apparatus measuring the sheet width at low speed, and FIG. 2D being a view of a weld that has been moved to a stopping position by the weld detecting apparatus.
Figure 3:
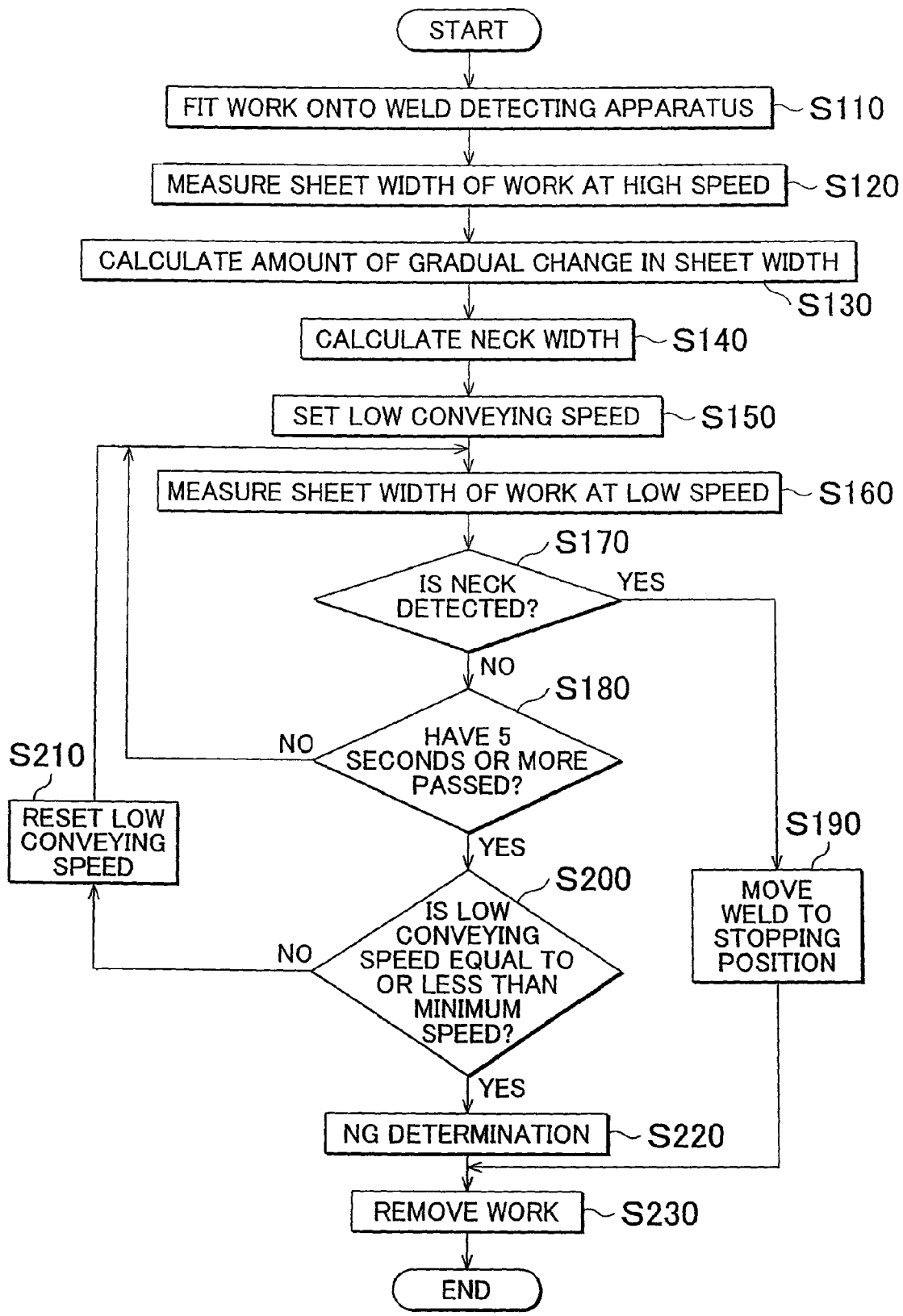
FIG. 3 is a flowchart illustrating an operation of the weld detecting apparatus according to the first example embodiment that detects a weld on a metal ring.

First, as shown in FIGS. 2A and 3, the work 100 is fitted onto the weld detecting apparatus 1 (S110). More specifically, the work 100 is wound around the driving pulley 11 and the tension pulley 12.

Figure 2B:
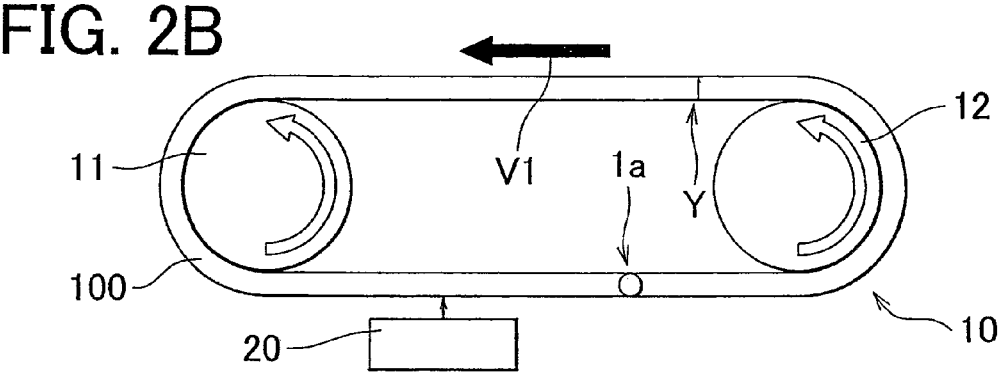

As shown in FIGS. 2B and 3, after fitting the work 100 onto the weld detecting apparatus 1, the sheet width H of the work is measured at high speed (S120). In this case, the weld detecting apparatus 1 conveys the work 100 at the conveying speed V1 by rotating the driving pulley 11 at high speed. Also, the weld detecting apparatus 1 conveys the work 100 a distance sufficiently longer than the circumferential length of the work and measures the sheet width H of the work.

After measuring the sheet width H of the work at high speed, the weld detecting apparatus 1 calculates the amount of gradual change C in the sheet width from the measurement results (S130). That is, the weld detecting apparatus 1 obtains the sheet width H of the work in step S120. The sheet width H is a numerical value necessary for calculating the amount of gradual change C in the sheet width.

After calculating the amount of gradual change C in the sheet width, the weld detecting apparatus 1 calculates the width L of the neck based on a correlation between the width L of the neck and the amount of gradual change C in the sheet width that has been obtained beforehand (S140).

After calculating the width L of the neck, the weld detecting apparatus 1 sets the low conveying speed V2 according to the width L of the neck (S150).

Figure 2C:
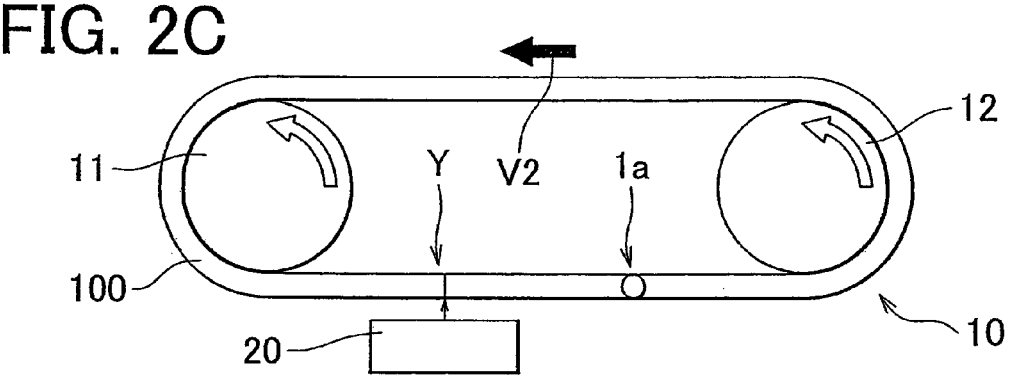

As shown in FIGS. 2C and 3, after setting the low conveying speed V2, the weld detecting apparatus 1 measures the sheet width H at the set low conveying speed V2 (S160). From this, the weld detecting apparatus 1 detects the neck 101.

Figure 2D:
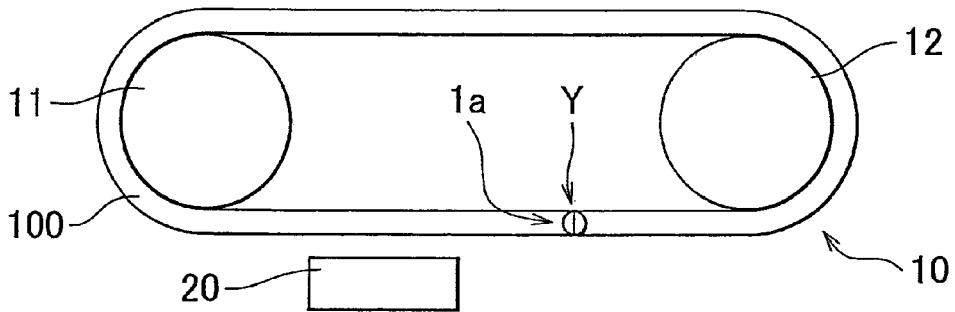

If the neck 101 is detected in step S170, the weld detecting apparatus 1 then conveys the work 100 so that the detected neck 101, i.e., the weld Y, moves to the stopping position 1a, as shown in FIGS. 2D and 3 (Yes in S170; S190). Then the work 100 is removed from the weld detecting apparatus 1 and detection of the weld Y ends (S230).

If, on the other hand, the neck 101 is not detected in step S170, the time elapsed after the sheet width H is measured at high speed (i.e., the time that it takes to progress from step S120 to step S170) is checked (i.e., No in S170). In this example embodiment, the elapsed time is measured by performing timer control with the weld detecting apparatus 1.

If at least five seconds have not passed after the start of the detection of the weld Y, detection of the neck 101 at low speed is then performed (No in S180).

If, on the other hand, at least five seconds have passed after the start of detection of the weld Y, whether the speed is equal to or less than a minimum speed is checked (Yes in S180).

Figure 15A:
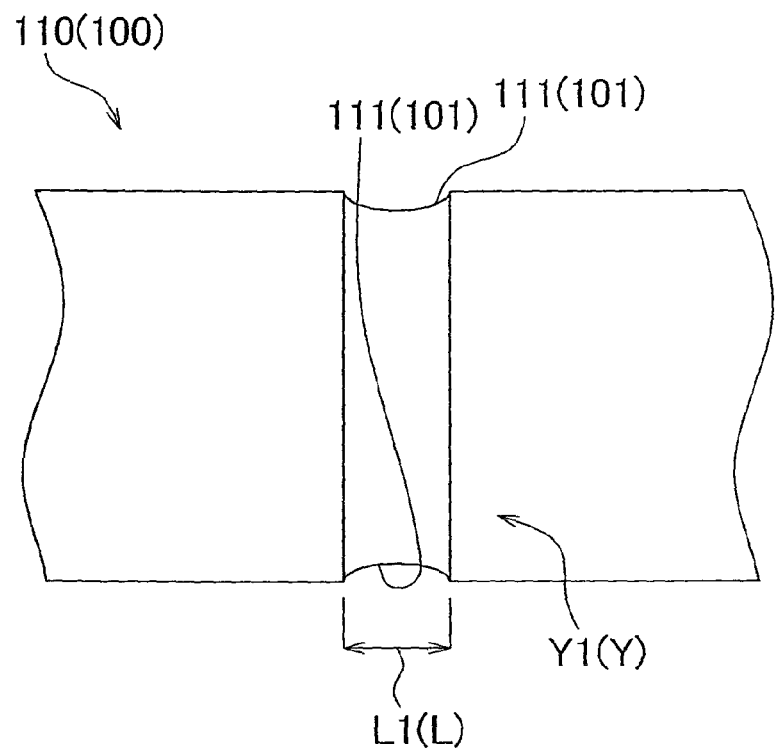
FIGS. 15A and 15B are enlarged side views of the neck of the metal ring, with FIG. 15A being a view of the neck of a metal ring with the smallest amount of elongation, and FIG. 15B being a view of the neck of a metal ring with the largest amount of elongation.

The minimum speed in the first example embodiment is the low conveying speed V2 that is set when measuring the neck 111 of the neck 110 with the smallest amount of elongation (see FIG. 15A).

If the low conveying speed V2 is higher than the minimum speed, the low conveying speed V2 is reset (No in S200; S210). At this time, the weld detecting apparatus 1 resets the currently set low conveying speed V2 to a slower speed. Then the weld detecting apparatus 1 detects the sheet width H at the reset conveying speed V2 (S160, S170). Accordingly, the weld Y can still be reliably detected even if, for example, a width L of the neck that is larger than the original width L of the neck is calculated due to an error occurring when the amount of gradual change C in the sheet width is measured.

If the low conveying speed V2 is equal to or less than the minimum speed, it is determined that the work 100 is such that the weld Y is unable to be detected (i.e., a NG determination) (Yes in S200; S220). At this time, the weld detecting apparatus 1 notifies a worker or the like according to a predetermined method that the weld Y is unable to be detected. One example of a method for performing such notification involves electrically connecting a predetermined display portion to the weld detecting apparatus 1 and indicating that a NG determination was made on the display portion. The work 100 is then removed from the weld detecting apparatus 1 and detection of the weld Y ends (S230).

In this way, the weld detecting method of the first example embodiment detects the weld Y on the work by detecting the neck 101 formed at the weld Y on the work when elongating the work 100 having the weld Y. Accordingly, the low conveying speed V2 can be set according to the width L of the neck, so the weld Y can be detected at a faster speed than it can be at the minimum speed, for example. That is, the conveying speed V2 when detecting the neck 101 formed at the weld Y can be optimally set, so the time that it takes to detect the weld Y on the work can be reduced. Also, the conveying speed V2 of the work when detecting the neck 101 can be optimally set even when an inexpensive sensor with long measurement intervals of the sheet width H of the work is used. That is, the time that it takes to detect the weld Y on the work can be reduced and the weld Y can be detected at low cost.

Also, the width L2 of the neck in the work 120 with the largest amount of gradual change C in the sheet width is approximately twice the length of the width L1 of the neck in the work 110 with the smallest amount of gradual change C in the sheet width, as described above. Therefore, when the measurement intervals of the detecting mechanism 20 are constant, the weld detecting apparatus 1 can set the low conveying speed V2 of the work 120 to a speed approximately twice the low conveying speed V2 of the work 110. That is, the time that it takes to detect the weld Y on the work can be reduced by approximately half depending on the amount of elongation of the work 100.

Also, when calculating the width L of the neck based on the correlation between the width L of the neck and the amount of gradual change C in the sheet width, the calculation of the width L of the neck and the detection of the neck 101 can be performed by one detecting mechanism 20. That is, it is not necessary to use a separate sensor and the like to calculate the width L of the neck. Therefore, the weld Y on the work can be detected at low cost.

Figure 15B:
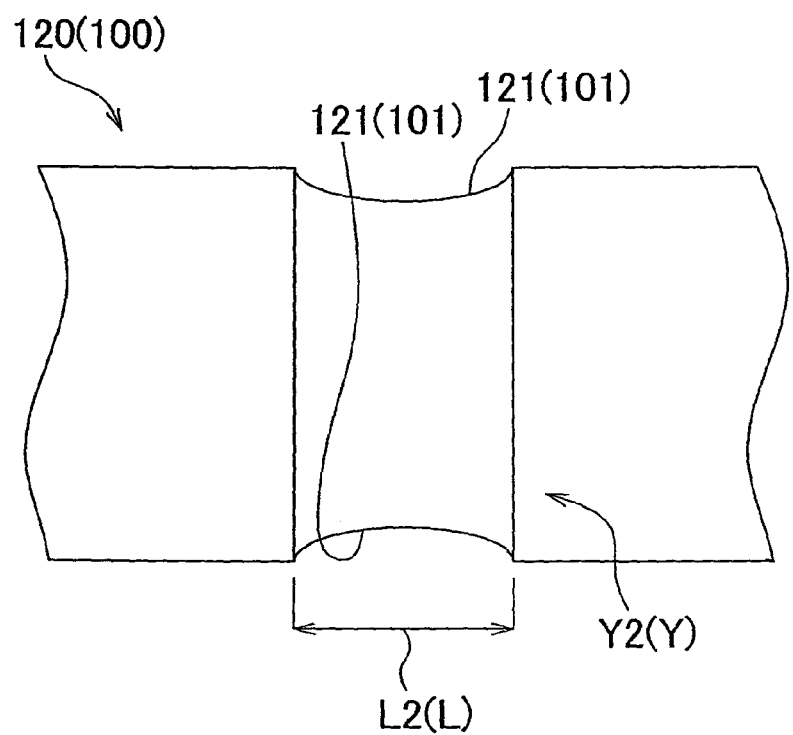

Next, the relationship between the width L of the neck and the amount of elongation of the work 100 will be described. As shown in FIGS. 15A and 15B, the width L2 of the neck in the work 120 is longer than the width L1 of the neck in the work 110.

Figure 16:
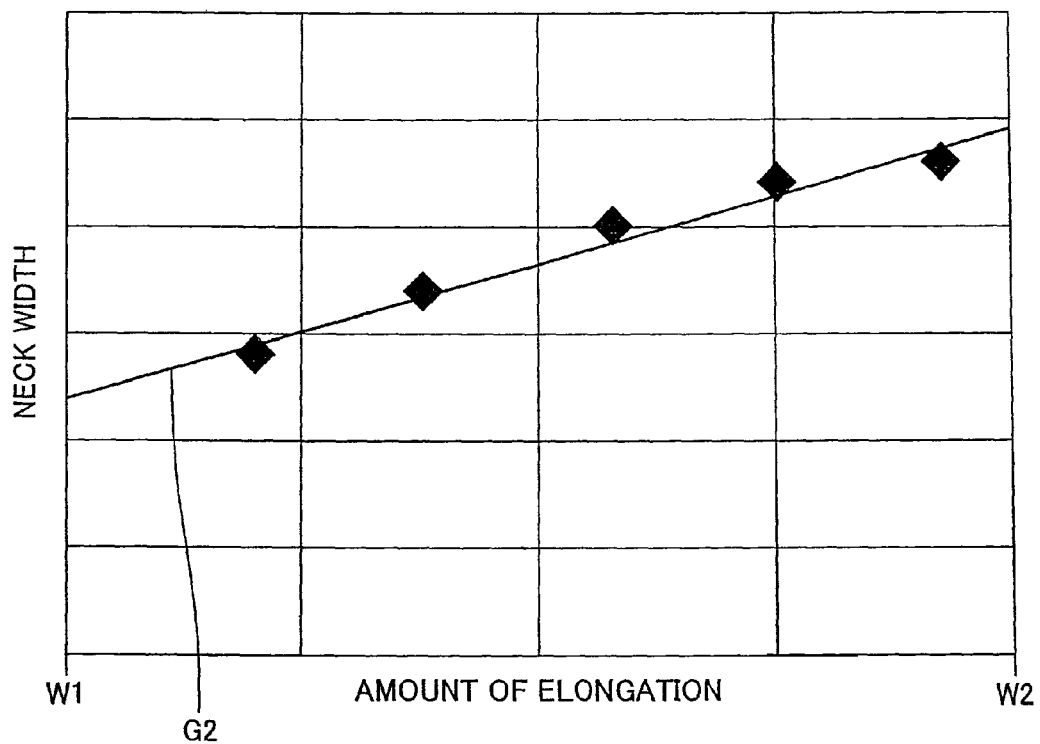
FIG. 16 is a graph showing the correlation between neck width and the amount of elongation.

FIG. 16 is a graph showing the test results from measuring the width L of the neck corresponding to works 100 with different amounts of elongation. The width L of the neck increases by increasing the amount of elongation of the work 100, i.e., by increasing the circumferential length of the work 100 (i.e., see the circumferential length W1 in FIG. 11 and the circumferential length W2 in FIG. 12). That is, it is evident that there is a correlation between the width L of the neck and the amount of elongation of the work (see graph G2 in FIG. 16).

Accordingly, the width L of the neck can be calculated based on the correlation between the width L of the neck and the amount of elongation of the work 100. That is, the low conveying speed V2 can be set by calculating the amount of elongation. In the weld detecting method of the first example embodiment, the width L of the neck may also be calculated based on a correlation between the width L of the neck and the amount of elongation that has been obtained beforehand.

In this case, the weld detecting apparatus 1 may also include a circumferential length measuring mechanism that calculates the circumferential length W of the work.

The circumferential length measuring mechanism measures the distance from the center point of the driving pulley 11 to the center point of the tension pulley 12, for example. Then the circumferential length measuring mechanism calculates the circumferential length W of the work by calculating the sum of the distance of twice the measured distance and the distance of one-half of the circumference of the driving pulley 11 and the tension pulley 12.

Also, the weld detecting apparatus 1 is configured to be able to calculate the width L of the neck based on the correlation between the width L of the neck and the amount of elongation that has been obtained beforehand.

The weld detecting apparatus 1 structured in this way first calculates the circumferential length W of the work using the circumferential length measuring mechanism when starting to detect the weld Y.

After measuring the circumferential length W of the work, the amount of elongation of the work 100 is calculated based on the circumferential length of the work before the work is elongated in the rolling process S5 (see FIG. 10). That is, the weld detecting apparatus 1 obtains the amount of elongation of the work 100 by measuring the circumferential length W of the work. The amount of elongation of the work 100 is a numerical value necessary to calculate the width L of the neck of the work 100. Then the weld detecting apparatus 1 calculates the width L of the neck based on the correlation between the width L of the neck and the amount of elongation of the work 100.

After calculating the width L of the neck, the low conveying speed V2 is calculated according to the width L of the neck, and the neck 101 is detected (i.e., steps S150 to S230).

Accordingly, the conveying speed V2 of the work when detecting the neck 101 can be optimally set, so the time that it takes to detect the weld Y on the work can be reduced.

When calculating the low conveying speed V2 by measuring the circumferential length W of the work, the sheet width H may be measured at low speed for the circumferential length of the work (i.e., for the measured circumferential length W) after the low conveying speed V2 has been calculated. Accordingly, the low conveying speed V2 can be reset quickly even if, for example, a width L of the neck that is larger than the original width L of the neck is calculated due to an error occurring when the amount of elongation is calculated.

Figure 17A:
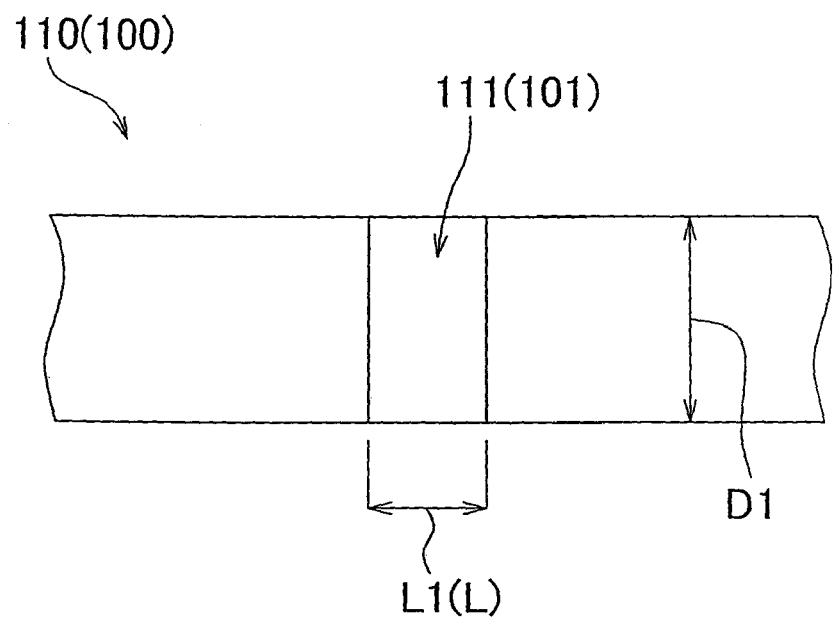
FIGS. 17A and 17B are enlarged plan views of the sheet thickness of the metal ring, with FIG. 17A being a view of the plate thickness of a metal ring with the smallest amount of elongation, and FIG. 17B being a view of the plate thickness of a metal ring with the largest amount of elongation.
Figure 17B:
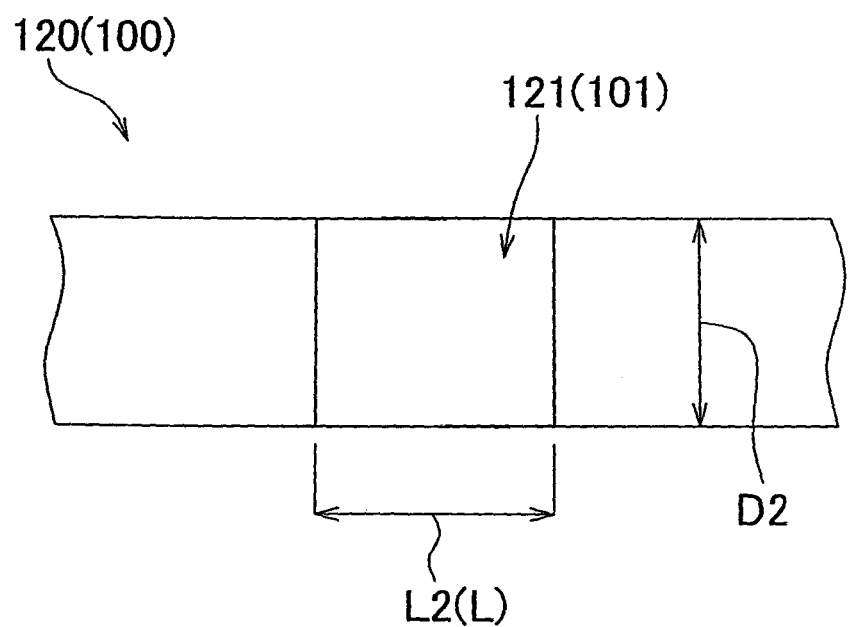

Next, the relationship between the sheet thickness. D and the neck 101 will be described. The sheet thickness D of the work is made thin by the rolling process S5 and the circumferential length adjusting process S6. At this time, the work 100 is plastically deformed such that the percent by which the sheet thickness D is made thinner and the percent by which the work 100 is elongated are the same percent. That is, there is a correlation between the amount of change in the sheet thickness D and the amount of elongation before and after the work 100 undergoes the rolling process S5 and the circumferential length adjusting, process S6. Therefore, as shown in FIG. 17, the width L2 of the neck in the work 120 in which the sheet thickness D2 is thin is longer than the width L1 of the neck in the work 110 in which the sheet thickness D1 is thick.

The width L of the neck can be calculated based on a correlation between the width L of the neck and the amount of change in the sheet thickness. D. That is, the low conveying speed V2 can be set by measuring the sheet thickness D. In the weld detecting method of the first example embodiment, the width L of the neck may also be calculated based on the correlation between the width L of the neck and the amount of change in the sheet thickness D.

In this case, the weld detecting apparatus 1 may also include a sheet thickness measuring mechanism that measures the sheet thickness D of the work.

A laser sensor such as that of the detecting mechanism 20, for example, may be used for the sheet thickness measuring mechanism.

Also, the weld detecting apparatus 1 may be configured so as to be able to calculate the width L of the neck based on the correlation between the width L of the neck and the amount of change in the sheet thickness D.

When the weld detecting apparatus 1 structured in this way starts to detect the weld Y, the sheet thickness D of the work is first measured using a measuring apparatus. At this time, even if the weld Y is skipped over, it will not affect the measurement results of the sheet thickness D, so the sheet thickness D is measured at a speed that is faster than the low conveying speed V2, such as the high conveying speed V1, for example.

After measuring the sheet thickness D of the work, the width L of the neck is calculated based on the correlation between the width L of the neck and the amount of change in the sheet thickness D that has been obtained beforehand. That is, the weld detecting apparatus 1 obtains the sheet thickness D of the work by measuring the sheet thickness D of the work. The sheet thickness D of the work is a numerical value necessary for calculating the amount of change in the sheet thickness D'.

After calculating the width L of the neck, the low conveying speed V2 is calculated according to the width L of the neck, and the neck 101 is detected (i.e., steps S150 to S230), as described above.

Accordingly, the conveying speed V2 of the work when detecting the neck 101 can be optimally set, so the time that it takes to detect the weld Y on the work can be reduced.

Incidentally, in the weld detecting method of the first example embodiment that detects the weld Y on the metal ring, the amount of time that has passed after the sheet width H is measured at high speed (i.e., the time that it takes to perform steps S120 to S170) is checked if the neck 101 is unable to be detected. However, the invention is not limited to this as long as a sheet width H equal to or greater than the circumferential length of the metal ring is able to be measured at the low conveying speed V2.

Next, the structure of the weld detecting apparatus 1 when detecting a weld Y on a metal band that is an elongated member extended in a band shape will be described. The work 100 that is a metal band is elongated by rolling after a plurality of metal sheets have been joined together by welding. As a result, a plurality of welds Y are formed on the work 100, as shown in FIG. 4B. However, the work will not be pulled and elongated, so the sheet width H of the work will not gradually change. That is, the sheet width H of the work will not change except for at the neck 101.

Figure 4A:
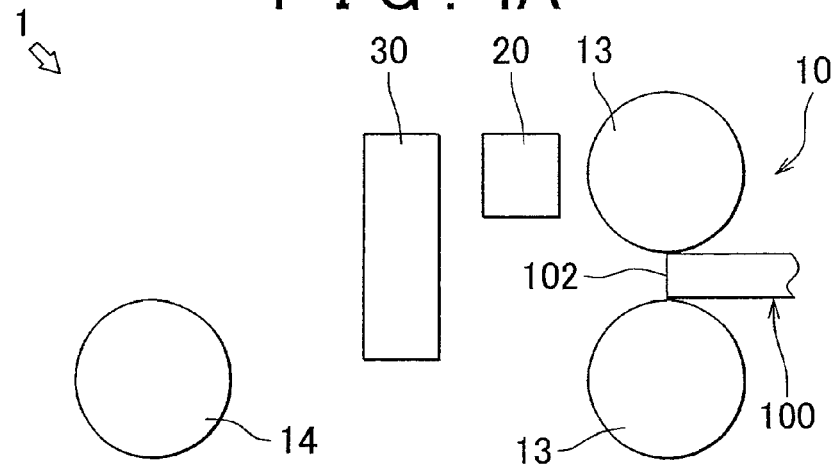
FIGS. 4A to 4C are side views of the operation of the weld detecting apparatus according to the first example embodiment that detects a weld on a metal band, with FIG. 4A being a view of a work fitted onto the weld detecting apparatus, FIG. 4B being a view of the weld detecting apparatus measuring the sheet width at high speed, and FIG. 4C being a view of the weld detecting apparatus measuring the sheet width at low speed.
Figure 4B:
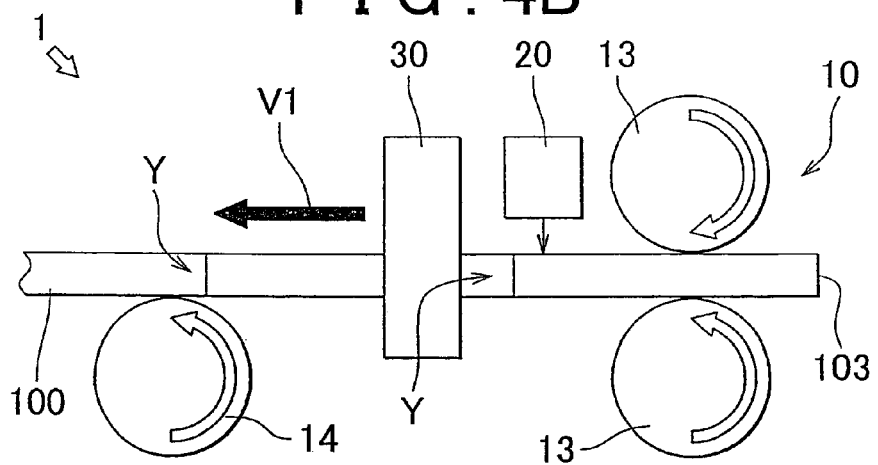

The weld detecting apparatus 1 includes the conveying mechanism 10, the detecting mechanism 20, and a length measuring mechanism 30, as shown in FIG. 4A.

Also, as shown in FIG. 4A, the conveying mechanism 10 includes a pair of first conveyance rollers 13 and a second conveyance roller 14. The pair of first conveyance rollers 13 are arranged sandwiching the sheet face of the work 100, and are configured so as to be able to rotate by a predetermined driving source. Also, a rotary encoder is mounted to one of the first conveyance rollers 13 (the upper first conveyance roller 13 in this example embodiment), and the rotation of the pair of first conveyance rollers 13 is monitored. The second conveyance roller 14 is formed in generally the same shape as the pair of first conveyance rollers 13, and is arranged a predetermined distanced away from the pair of first conveyance rollers 13 in the conveying direction of the work 100. Also, the second conveyance roller 14 is configured so as to be able to rotate at the same rotation speed as the pair of first conveyance rollers 13.

The detecting mechanism 20 is arranged between the pair of first conveyance rollers 13 and the second conveyance roller 14, and so as not to interfere when the work 100 is moved on the first conveyance rollers 13 and the second conveyance roller 14. The detecting mechanism 20 is formed by a non-contact laser sensor, and configured to be able to measure the sheet width H of the work.

The length measuring mechanism 30 is also arranged between the pair of first conveyance rollers 13 and the second conveyance roller 14, and so as not to interfere when the work 100 is moved on the first conveyance rollers 13 and the second conveyance roller 14. The length measuring mechanism 30 is formed by a non-contact laser sensor, and is configured to be able to measure the length of the work in the longitudinal direction (i.e., the length of the work in the conveying direction).

The high conveying speed V1 is set to a predetermined speed. Also, the measurement intervals of the detecting mechanism 20 are set to the shortest measurement intervals at which the detecting mechanism 20 is capable of taking, measurements. Also, the weld detecting apparatus 1 is configured so as to be able to calculate the width L of the neck based on a correlation between the width L of the neck and the amount of elongation (see graph G2 in FIG. 16).

A weld detecting method according to the first example embodiment that is performed using the weld detecting apparatus 1 having the structure described above will now be described.

Figure 5:
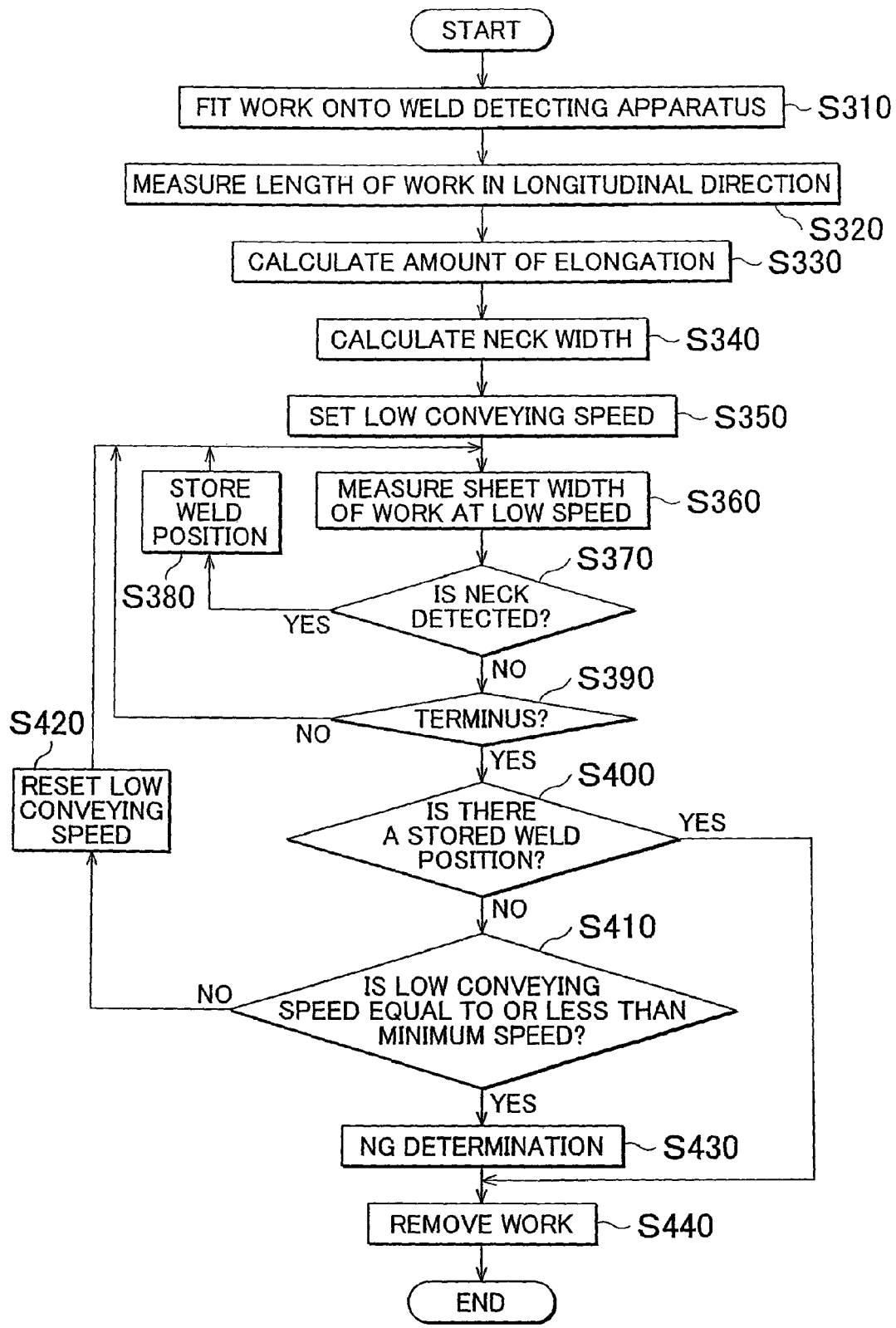
FIG. 5 is a flowchart illustrating an operation of the weld detecting apparatus according to the first example embodiment that detects a weld on a metal band.

First, the work 100 is fitted onto the weld detecting apparatus 1, as shown in FIGS. 4A and 5 (S310). More specifically, the work 100 is set with a starting end 102 of the work 100 sandwiched in between the first conveyance rollers 13.

Next, the weld detecting apparatus 1 conveys the work 100 at high speed by the conveying mechanism 10, and measures the length of the work in the longitudinal direction with the length measuring mechanism 30, as shown in FIGS. 4B and 5 (S320).

After measuring the length of the work in the longitudinal direction, the weld detecting apparatus 1 calculates the amount of elongation of the work 100 based on the length of the work in the longitudinal direction before the work 100 is elongated in a rolling process (S330).

After calculating the amount of elongation of the work 100, the width L of the neck is calculated based on a correlation between the width L of the neck and the amount of elongation of the work 100 that has been obtained beforehand (S340).

After calculating the width L of the neck, the low conveying speed V2 is set according to the width L of the neck (S350).

Figure 4C:
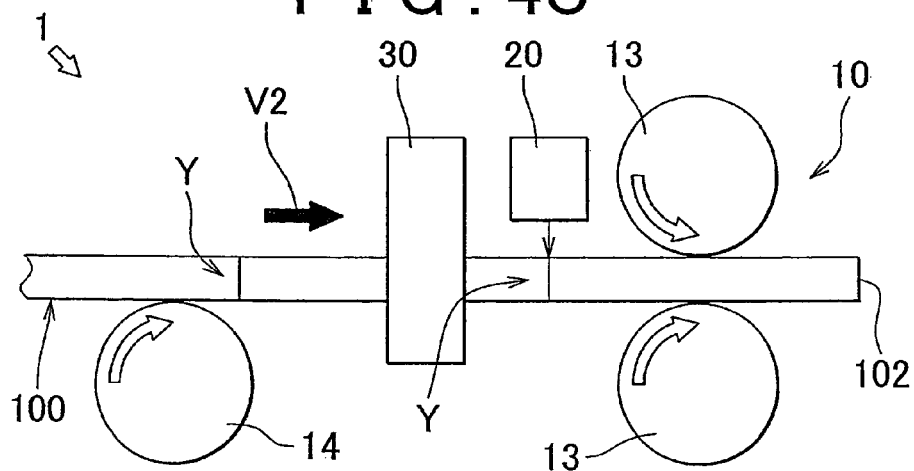

As shown in FIGS. 4C and 5, after setting the low conveying speed V2, the conveying mechanism 10 measures the sheet width H at the set conveying speed V2 (S360). At this time, the conveying mechanism 10 conveys the work 100 in the direction opposite the direction in which the work is conveyed when the length of the work is measured in the longitudinal direction.

If the neck 101 is detected in step S370, the position of the detected neck 101, i.e., the position of the weld Y, is stored (Yes in S370; S380). Then the sheet width H of the work is measured at low speed up to a terminus 103 of the work (No in S390).

After detection of the neck 101 up to the terminus 103 of the work, a check is performed in step S400 to verify whether the position of the neck 101 is stored (Yes in S390).

If the position of the weld Y has been stored in step S380, a worker or the like is notified of the position of the weld Y. One example of a method for performing such notification involves providing a button that is electrically connected to the weld detecting apparatus 1, and conveying the work 100 such that the welds Y come to be situated at a predetermined position in order each time the button is pushed. The work 100 is then removed from the weld detecting apparatus 1 and detection of the weld Y ends (S440).

If, on the other hand, the position of the weld Y has not been stored in step S380, a check is performed to verify whether the low conveying speed V2 is equal to or less than the minimum speed (No in S400).

If the low conveying speed V2 is higher than the minimum speed, the low conveying speed V2 is reset (No in S410; S420). At this time, the weld detecting apparatus 1 resets the currently set low conveying speed V2 to a slower speed. Then detection of the neck 101 is performed at the reset conveying speed V2 (S360, S370).

If the low conveying speed V2 is equal to or less than the minimum speed, it is determined that the work 100 is such that the weld Y is unable to be detected (i.e., a NG determination) (Yes in S410; S430). At this time, the weld detecting apparatus 1 notifies a worker or the like according to a predetermined method that the weld Y is unable to be detected. The work 100 is then removed from the weld detecting apparatus 1 and detection of the weld Y ends (S440).

In this way, the weld detecting method of the first example embodiment detects the weld Y on the work by detecting the neck 101 formed at the weld Y on the work, by detecting while conveying the work 100 at a predetermined conveying speed, when elongating the work 100 having the weld Y. Accordingly, the low conveying speed V2 can be set according to the width L of the neck. That is, the conveying speed V2 when detecting the neck 101 formed at the weld Y can be optimally set, so the time that it takes to detect the weld Y on the work can be reduced.

Incidentally, the weld detecting method of the first example embodiment when detecting a metal band may also calculate the width L of the neck based on a correlation between the width L of the neck and the amount of change in the sheet thickness D before and after the work 100 is roiled, and then set the low conveying speed V2 according to this width L of the neck. Also, the low conveying speed V2 may be set based on a correlation between the width L of the neck and an amount of gradual change C in the sheet width. However, when the work is elongated by rolling, as with the metal band in the first example embodiment, i.e., when the work is not elongated by pulling, the sheet width H of the work will not gradually change. In this case, the width L of the neck is calculated based on a correlation between the width L of the neck and either the amount of elongation of the work 100 or the amount of change in the sheet thickness D, and the low conveying speed V2 is set according to this width L of the neck.

Also, in the weld detecting method of the first example embodiment, the width L of the neck is calculated based on a correlation between the width L of the neck and at least one of the amount of elongation of the work 100, the amount of change in the sheet thickness D, or the amount of gradual change C in the sheet width, but the invention is not limited to this. That is, in the weld detecting method, the width L of the neck may also be calculated based on all of the correlations, i.e., the correlation between the width L of the neck and the amount of elongation of the work 100, the correlation between the width L of the neck and the amount of change in the sheet thickness D, and the correlation between the width L of the neck and the amount of gradual change C in the sheet width. In this case, the sheet width H, the sheet thickness D, and the amount of elongation of the work 100 are all measured in processes (S120 and S320) for measuring the work 100 before calculating the width L of the neck.

Accordingly, even if the width L of the neck is difficult to calculate by the amount of elongation of the work 100, for example, the width L of the neck can still be reliably calculated by the amount of change in the sheet thickness D and the amount of gradual change C in the sheet width. That is, the conveying speed V2 when detecting the neck 101 can be optimally set, so the neck 101 can be detected with one measurement. Therefore, the neck 101 can be detected without resetting the low conveying speed V2, so it is possible to prevent the time that it takes to detect the weld Y from increasing.

In this way, the process of calculating the width L of the neck (i.e., steps S140 and S340) functions as a calculating process of i) obtaining in advance at least one correlation, from among a correlation between the width L of the neck and the amount of elongation of the work 100 and a correlation between the width L of the neck and the amount of change in at least one of the sheet width H of the work or the sheet thickness D of the work before and after the elongation of the work 100, and ii) calculating the width L of the neck based on the at least one correlation by obtaining at least one of the sheet thickness D, the sheet width H, or the amount of elongation of the work 100 from the obtained at least one correlation.

Also, the process of setting the low conveying speed V2 (i.e., steps S150 and S350) functions as a setting process of setting the conveying speed V2 when detecting the neck 101, according to the width L of the neck calculated in the process for calculating the width L of the neck (i.e., steps S140 and S340).

Also, the process of measuring the sheet width H of the work at low speed (i.e., steps S160 and S360) functions as a detecting process of detecting the neck 101 by measuring the sheet width H of the work at predetermined intervals while conveying the work 100 at the conveying speed V2 of the work that is set in the process of setting the low conveying speed V2 (i.e., steps S150 and S350).

Accordingly, the conveying speed V2 of the work when detecting the neck 101 formed at the weld Y can be optimally set, so the time that it takes to detect the weld Y on the work can be reduced.

Incidentally, the low conveying speed V2 in the weld detecting method enables the time that it takes to detect the weld Y on the work to be reduced, so the low conveying speed V2 is preferably a fast speed at which the neck 101 is still able to be detected.

Also, in resetting the low conveying speed V2, the detecting mechanism 20 just needs to be able to detect the neck 101 of a very small width. That is, the measurement intervals of the detecting mechanism 20 may be reset, or the low conveying speed V2 and the measurement intervals of the detecting mechanism 20 may be reset.

For example, when the measurement intervals of the detecting mechanism 20 are able to be even shorter, the measurement intervals of the detecting mechanism 20 may be shortened when resetting the low conveying speed V2. Accordingly, the neck 101 of a very small width can be detected without changing the low conveying speed V2. In this case, the low conveying speed V2 may be increased as long as the neck 101 of a very small width can still be detected.

In this way, the process of resetting the low conveying speed V2 (i.e., steps S210 and S420) functions as a resetting step of resetting at least either the measurement intervals of the sheet width H of the work or the conveying speed V2 of the work when detecting the neck 101, when the neck 101 is unable to be detected in the process of measuring the sheet width H of the work at low speed (i.e., steps S160 and S360). Also, the process of measuring the sheet width H of the work at low speed (i.e., steps S160 and S360) detects the neck 101 by measuring the sheet width H of the work at the measurement intervals and the conveying speed V2 that have been reset in the process of resetting the measurement intervals and the low conveying speed V2 (i.e., steps S210 and S420). As a result, it is possible to reliably detect the weld Y even if an error occurs in the calculation of the width L of the neck, for example.

Next, the weld detecting apparatus 1 that detects a weld Y using a weld detecting method according to a second example embodiment of the invention will be described with reference to the drawings.

The structure of a weld detecting apparatus 1' in the second example embodiment is different when detecting a weld Y on a work 100 formed in an annular shape, such as a metal ring, for example, than when detecting a weld Y on a work 100 formed in a band shape, such as a metal band, for example.

Hereinafter, the weld detecting apparatus 1' when detecting a weld Y on a metal ring will be described. The weld detecting apparatus 1' is configured similar to the weld detecting apparatus 1 in the first example embodiment shown in FIG. 1, except for that the structure of the detecting mechanism 20 is different.

The detecting mechanism 20 is configured to be able to measure the sheet width H of the work and output the detection results via analog output or digital output. Therefore, the detecting mechanism 20 is configured to be able to measure at high speed using analog output, as well as measure accurately without being affected by noise using digital output. Also, the measurement intervals with analog output and the measurement intervals with digital output are both set to the smallest measurement intervals at which the detecting mechanism 20 is capable of taking measurements. The measurement intervals with analog output are set shorter than the measurement intervals with digital output.

In the second example embodiment, the conveying speed of the work when detecting the neck 101 when measuring the sheet width H using analog output will be referred to as the "high conveying speed V1". Also, in the second example embodiment, the conveying speed of the work when detecting the neck 101 when measuring the sheet width H using digital output will be referred to as the "low conveying speed V2".

The high conveying speed V1 and the low conveying speed V2 are each set to predetermined speeds at which the width L1 of the neck in a work with the smallest amount of elongation can be calculated. Here, the measurement intervals with analog output are shorter than the measurement intervals with digital output, as described above, so the high conveying speed V1 is faster than the low conveying speed V2.

A weld detecting method according to the second example embodiment that is performed using the weld detecting apparatus 1' having the structure described above will now be described.

Figure 6:
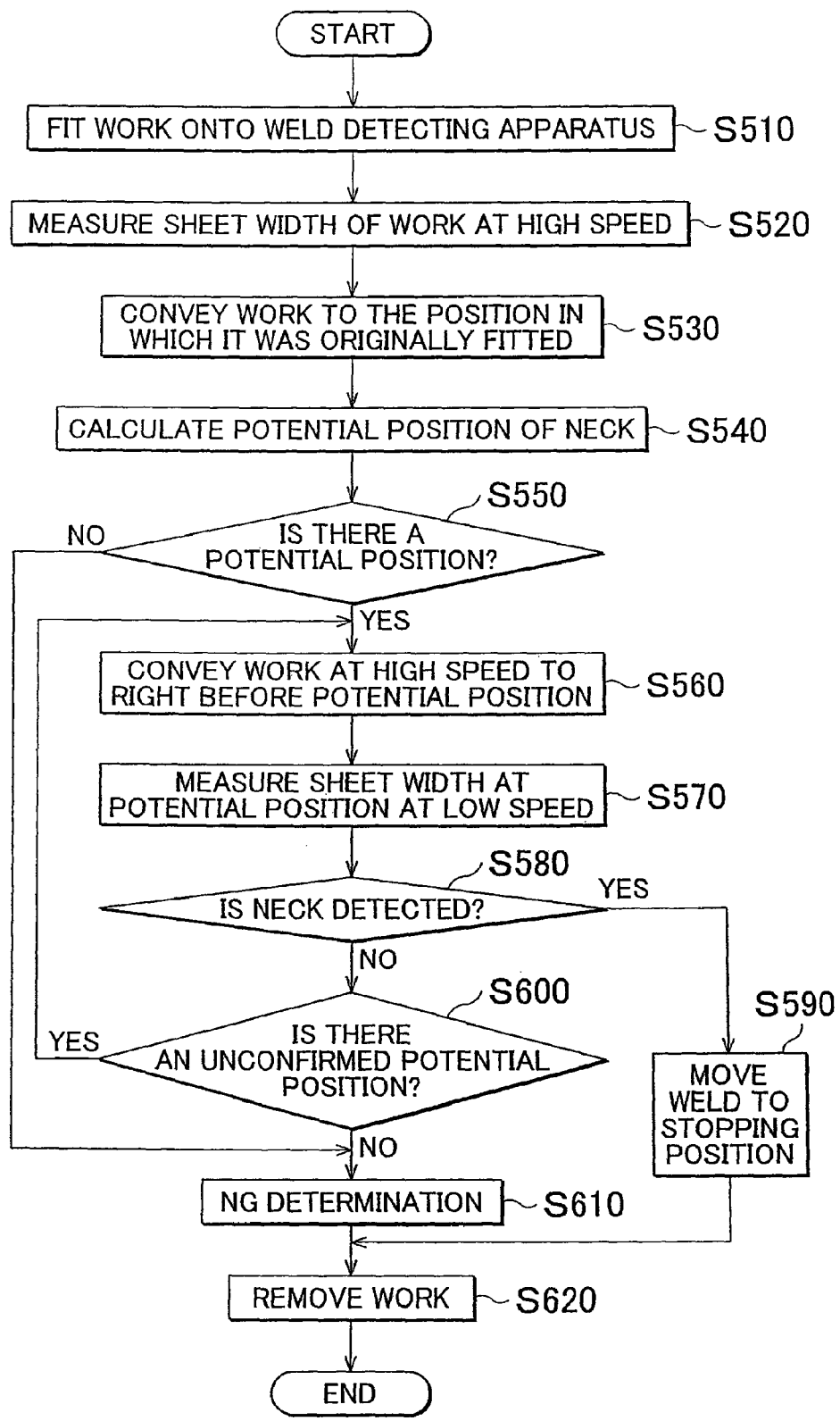
FIG. 6 is a flowchart illustrating an operation of a weld detecting apparatus according to a second example embodiment that detects a weld on a metal ring.

First, the work 100 is fitted onto the weld detecting apparatus 1', as shown in FIGS. 2A and 6 (S510).

After fitting the work 100 onto weld detecting apparatus 1', the sheet width H of the work is measured at high speed, as shown in FIGS. 2B and 6 (S520). At this time, the detecting mechanism 20 measures the sheet width H using analog output. Also, the weld detecting apparatus 1' conveys the work 100 for a distance that is sufficiently longer than the circumferential length of the work, and measures the sheet width H of the work.

Here, in the measurement results of the analog output, the position of the neck 101 may be erroneously detected due to the affect of noise or the like.

After measuring the sheet width H of the work at high speed, the work 100 is conveyed to the position in which it was originally fitted (S530). That is, the driving pulley 11 of the conveying mechanism 10 is rotated in reverse and the work 100 is conveyed the same distance that it is conveyed when the sheet width H is measured at high speed (S520). At this time, the sheet width H is not measured by the detecting mechanism 20, so the weld detecting apparatus 1' conveys the work 100 at a speed faster than the high conveying speed V1.

Figure 7:
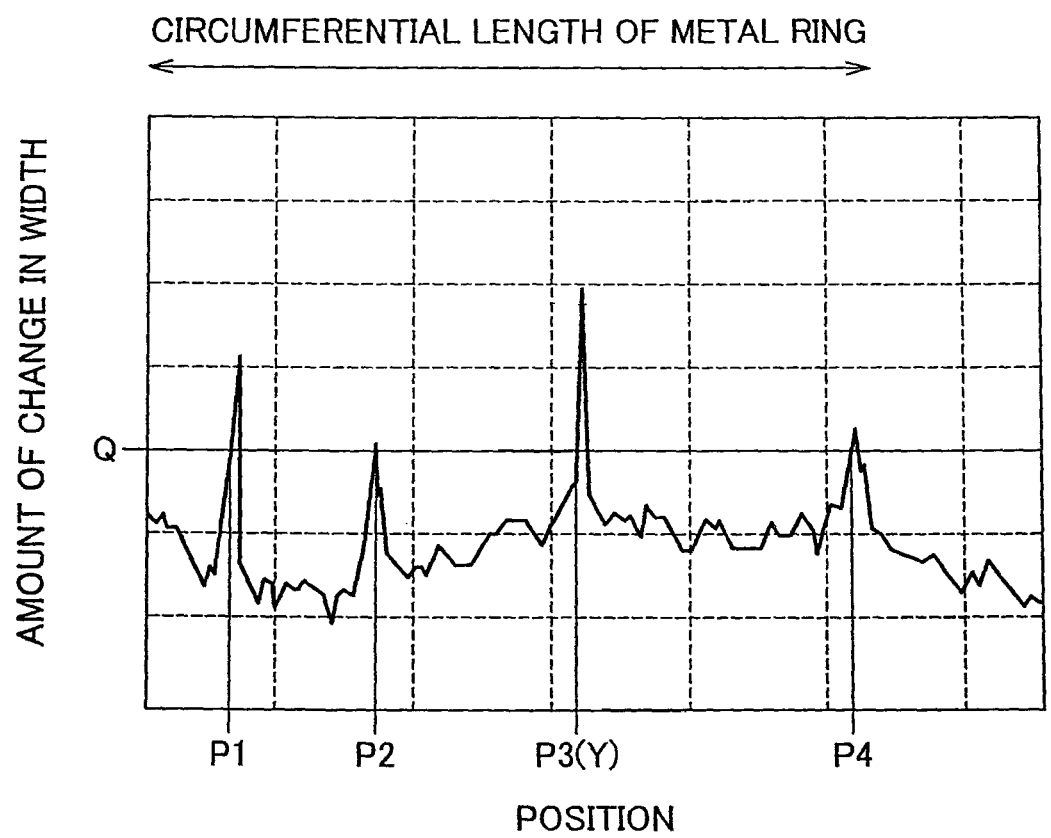
FIG. 7 is a graph showing the results from measuring the sheet width of the work at high speed when calculating potential positions.
Figure 8A:
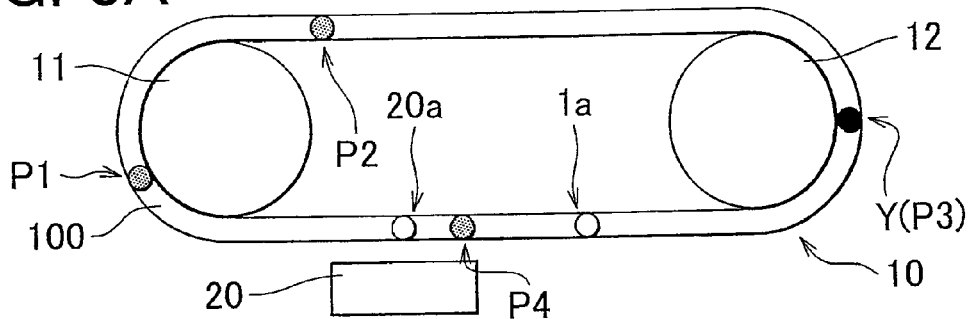
FIGS. 8A to 8D are side views of the operation of the weld detecting apparatus according to the second example embodiment that detects a weld on a metal ring, with FIG. 8A being a view of the weld detecting apparatus calculating potential positions, FIG. 8B being a view of the weld detecting apparatus measuring the sheet width of a potential position at low speed, FIG. 8C being a view of the weld detecting apparatus measuring the sheet width of a weld at low speed.

After the work 100 has been conveyed to the position in which it was originally fitted, potential positions of the neck 101 are calculated (S540). More specifically, as shown in FIG. 7, when measuring the sheet width H at high speed (S520), positions at which the amount of change in the sheet width H is large are calculated. Therefore, a threshold value Q is provided for the amount of change in the sheet width H, and the positions where this threshold value Q is exceeded are stored as potential positions. In this example embodiment, points P1 to P4 are potential positions, as shown in FIGS. 7 and 8A.

Incidentally, hereinafter, the points P1 to P4 will be referred to as "potential positions P1 to P4". Also, in the measurement results shown in FIG. 7, potential positions P1, P2, and P4 are portions where the amount of change has become large due to the affect of noise or the like. Also, the potential position P3 is a portion where the amount of change has become large due to the neck 101, i.e., the potential position P3 is the weld Y.

Also, hereinafter, the position where the sheet width H of the work is measured by the detecting mechanism 20 will be referred to as the "measuring position 20a".

As shown in FIG. 6, if a potential position is not detected in step S540, it is determined that the work 100 is such that the weld Y is unable to be detected (i.e., a NG determination) (No in S550; S610). At this time, the weld detecting apparatus 1' notifies a worker or the like according to a predetermined method that the weld Y is unable to be detected. The work 100 is then removed from the weld detecting apparatus 1' and detection of the weld Y ends (S620).

Figure 8B:
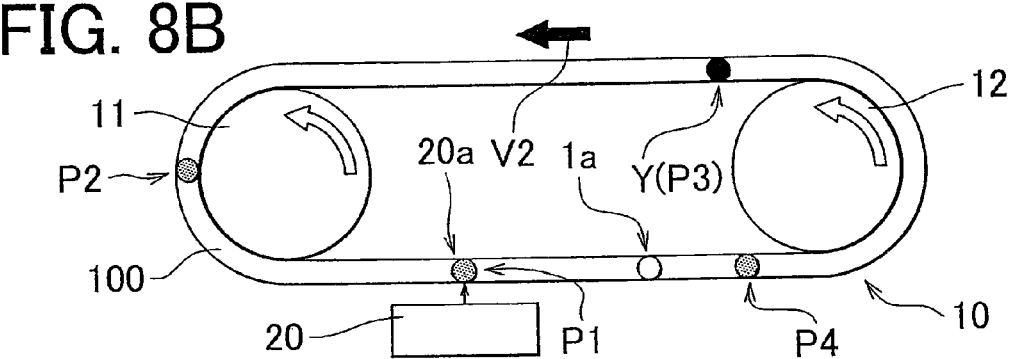

If, on the other hand, the potential positions P1 to P4 are detected in step S540, the work 100 is conveyed at high speed such that the potential position P1 calculated first comes to be situated at the measuring position 20a, as shown in FIGS. 6 and 8B (Yes in S550; S560). At this time, the sheet width H is not measured by the detecting mechanism 20, so the weld detecting apparatus 1' conveys the work 100 at a faster speed than the high conveying speed V1.

After the work 100 has been conveyed at high speed, the sheet width H of the potential position P1 is measured at low speed (S570). At this time, the sheet width H of the potential position P1 is measured using digital output. As a result, whether the potential position is the neck 101 or just an area that has been affected by noise or the like becomes evident. At this time, the weld detecting apparatus 1' measures the sheet width H for a predetermined distance from the potential position P1. In the measurement results shown in FIG. 7, the weld detecting apparatus 1' determines that the potential position P1 is due to the affect of noise or the like.

If it is determined in step S570 that the potential position P1 is due to the affect of noise or the like, a check is performed to verify whether there are any unconfirmed potential positions (No in S580). In this way, the weld detecting apparatus 1' eliminates those potential positions, from among the potential positions P1 to P4, that have been erroneously detected due to the affect of noise or the like. The measurement results shown in FIG. 7 verify the potential positions P2 to P4 as unconfirmed potential positions.

Figure 8C:
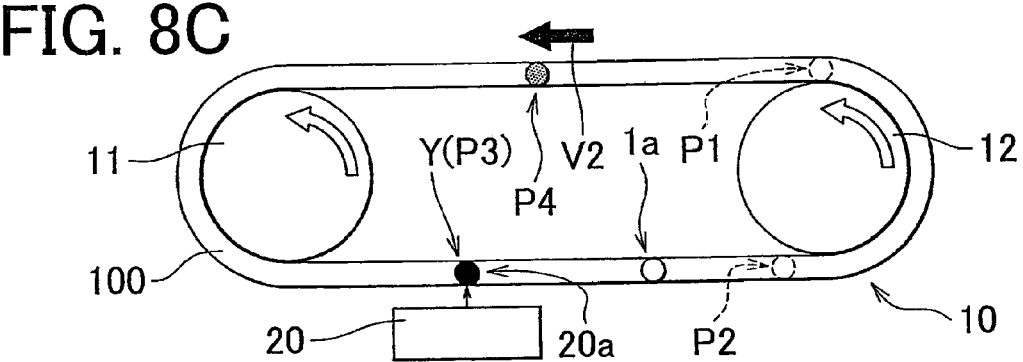
Figure 8D:
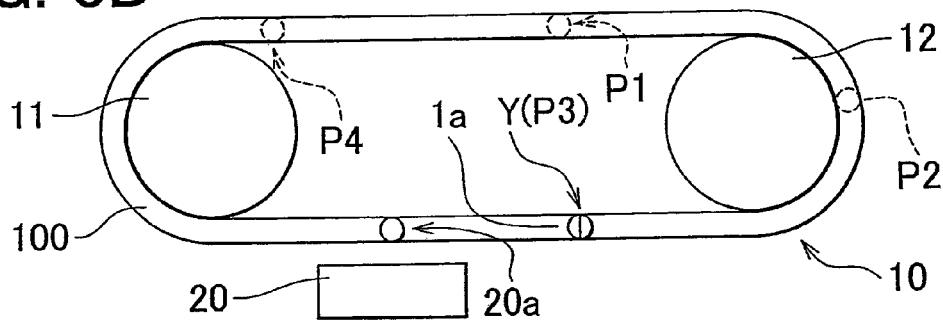

When there are unconfirmed potential positions P2 to P4, the work 100 is conveyed at a faster speed than the high conveying speed V1 such that the potential position P2 calculated next after the potential position P1 that has been determined to be due to the affect of noise or the like comes to be situated at the measuring position 20a (Yes in S600; S560). Then the sheet width H of the potential position P2 is measured at low speed using the digital output of the detecting mechanism 20 (S570). In the measurement results shown in FIG. 7, the sheet width H of the potential position P2 is measured at low speed and it is determined that the potential position P2 is due to the affect of noise or the like. Also, as shown in FIG. 8C, the work 100 is conveyed at a faster speed than the high conveying speed V1 such that the potential position P3 comes to be situated at the measuring position 20a, and the sheet width H is measured at low speed.

When the potential position P3 is determined to be the neck 101 when the sheet width H of the potential position P3 is measured in step S570, the potential position P3 that has been determined to be the neck 101 is moved to a stopping position 1a and detection ends (Yes in S580; S590). Then the work 100 is removed from the weld detecting apparatus 1' and detection of the weld Y ends (S620).

Incidentally, when the work 100 is a metal ring, one weld Y is formed on the work 100. Therefore, when the weld detecting apparatus 1' detects the weld Y, it is determined that the remaining potential position P4 of the weld is due to the affect of noise or the like, so the sheet width H is not measured there.

If, on the other hand, there are no unconfirmed potential positions, it is determined that the work 100 is such that the weld Y is unable to be detected (i.e., a NG determination) (No in S600; S610). At this time, the weld detecting apparatus 1' notifies a worker or the like according to a predetermined method that the weld Y is unable to be detected. The work 100 is then removed from the weld detecting apparatus 1' and detection of the weld Y ends (S620).

Accordingly, in the detection of the weld Y on the work, the area where detection of the neck 101 is performed can be decreased by the potential positions. In other words, the sheet width H is measured at low speed only at the potential positions, so the time that it takes to detect the weld Y on the work can be reduced. Also, even if an inexpensive sensor in which the measurement intervals of the sheet width H of the work are long is used, detection of the neck 101 is performed only at the potential positions. Also, in calculating the potential positions and in calculating the weld Y, the sheet width H of the work is measured, so the weld Y can be detected with a single sensor. That is, the time that it takes to detect the weld Y on the work can be reduced, while detection of the weld Y can be performed at low cost.

Next, the structure of the weld detecting apparatus 1' when detecting a weld Y on a metal band will be described. Incidentally, the metal band in this second example embodiment has a plurality of welds Y formed on it, similar to the metal band in the first example embodiment.

The weld detecting apparatus 1' has a structure similar to the weld detecting apparatus 1 in the first example embodiment shown in FIG. 4, except that the length measuring mechanism 30 is not provided and the structure of the detecting mechanism 20 is different.

The detecting mechanism 20 is configured to be able to measure the sheet width H of the work using analog output and digital output, similar to the detecting mechanism 20 of the weld detecting apparatus 1' that detects the weld Y on the metal ring in the second example embodiment. Also, the measurement intervals with analog output and the measurement intervals with digital output are both set to the smallest measurement intervals at which the detecting mechanism 20 is capable of taking measurements. The measurement intervals with analog output are set shorter than the measurement intervals with digital output.

The high conveying speed V1 and the low conveying speed V2 are each set to predetermined speeds at which the width L1 of the neck in a work with the smallest amount of elongation can be calculated.

A weld detecting method according to the second example embodiment that is performed using the weld detecting apparatus 1' having the structure described above will now be described.

Incidentally, the processes from the process of fitting the work 100 onto the weld detecting apparatus 1' up to the process of measuring the sheet widths H of potential positions (S710 to S760) are the same as the processes from the process of fitting the work 100 of the metal ring onto the weld detecting apparatus 1' up to the process of measuring the sheet widths H of potential positions (S510 to S560), except for that the work 100 is conveyed for a distance that is sufficiently longer than the length of the work in the longitudinal direction. Therefore, a description of the processes from the process of fitting the work 100 onto the weld detecting apparatus 1' up to the process of measuring the sheet widths H of potential positions (i.e., step S710 to S770) will be omitted.

Figure 9:
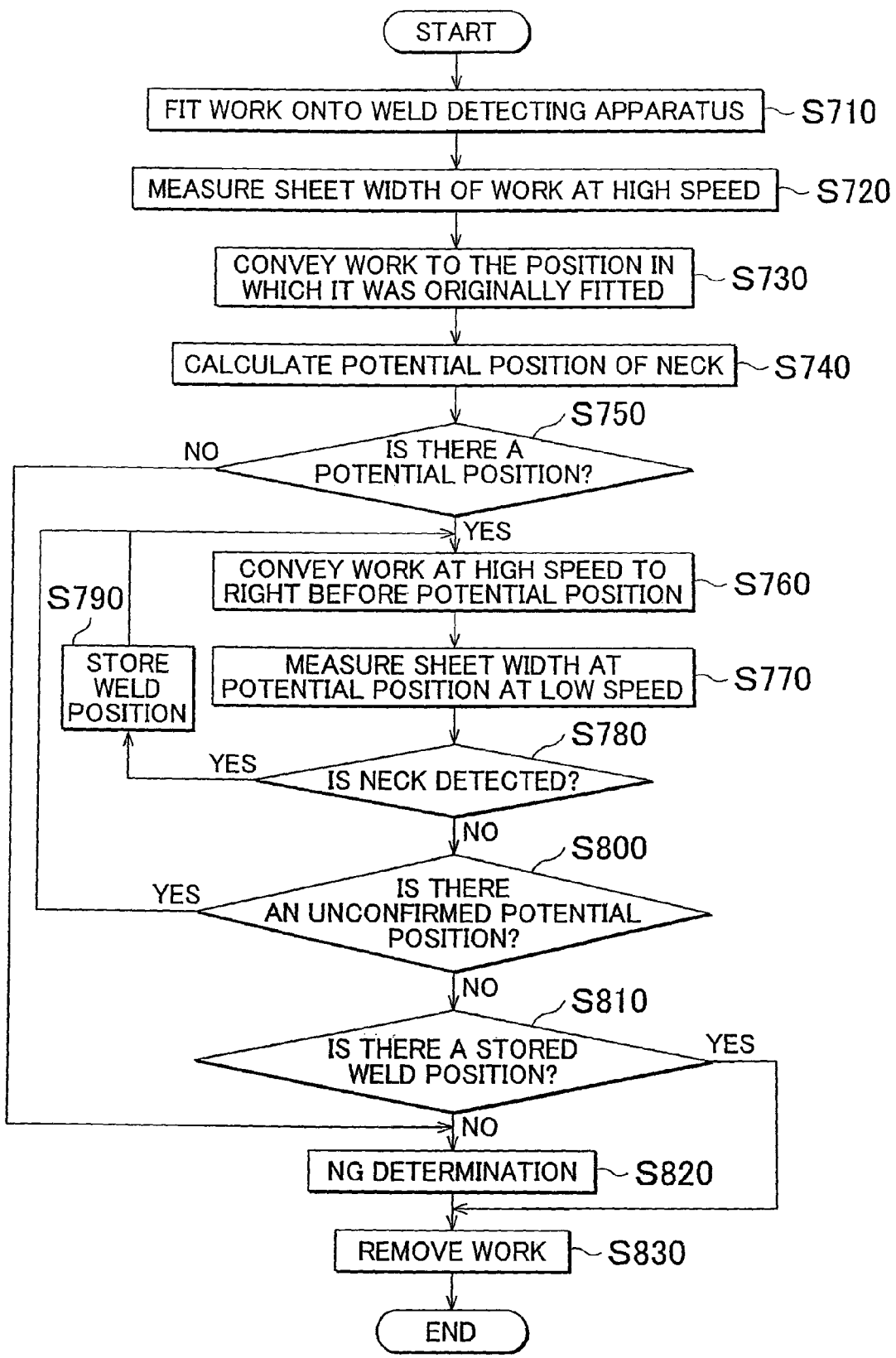
FIG. 9 is a flowchart illustrating an operation of the weld detecting apparatus according to the second example embodiment that detects a weld on a metal band.

As shown in FIG. 9, if it is determined in step S770 that a potential position is a neck 101, that position is stored as a position of a weld Y (Yes in S780; S790).

If, on the other hand, it is determined in step S770 that a potential position is not a neck 101, i.e., if it is determined that a potential position is due to the affect of noise or the like, a check is performed to verify whether there are any unconfirmed potential positions (No in S800).

If there are unconfirmed potential positions, the work 100 is conveyed at a faster speed than the high conveying speed V1 such that the next calculated potential position after the potential position that has been determined to be due to the affect of noise or the like comes to be situated at the measuring position 20a (Yes in S800; S760). Then the sheet width H of the potential position is measured at low speed using the digital output of the detecting mechanism 20 (S770).

If, on the other hand, there are no unconfirmed potential positions, then a check is performed to verify whether the position of a weld Y is stored. If a position determined to be the neck 101 is stored, a worker or the like is notified according to a predetermined method that the position of the neck 101 is a weld Y (Yes in S810).

If, on the other hand, a position determined in step S770 to be a neck 101 is not stored, then it is determined that the work 100 is such that the weld Y is unable to be detected (No in S810; S820). At this time, the weld detecting apparatus 1' notifies a worker or the like according to a predetermined method that the weld Y is unable to be detected. The work 100 is then removed from the weld detecting apparatus 1' and detection of the weld Y ends (S830).

In this way, the process of calculating the potential positions of the neck 101 (i.e., steps S540 and S740) functions as a calculation process of calculating potential positions of the neck 101 by measuring the sheet width H of the work, while conveying the work 100 at the high conveying speed V1 that is faster than the conveying speed V2 when detecting the neck 101.

Also, the process of measuring the sheet width H of the potential positions at low speed (i.e., steps S570 and S770) functions as a detecting process of detecting the neck 101 by measuring the sheet width H of potential positions calculated by the process of calculating the potential positions of the neck 101 (i.e., steps S540 and S740), at the conveying speed V2 of the work when detecting the neck 101.

Accordingly, in the detection of the weld Y on the work, the area where detection of the neck 101 is performed can be reduced, so the time that it takes to detect the weld Y on the work can be reduced.

Incidentally, in the weld detecting method of the second example embodiment, when measuring the length of the work in the longitudinal direction before calculating the potential positions, the work 100 may also be conveyed the measured length.

Also, in the weld detecting method of the second example embodiment, analog output is used when measuring the sheet width H when calculating a potential position, and digital output is used when measuring the sheet width H of a potential position. However, the invention is not limited to this.

For example, analog output may be used when measuring the sheet width H when calculating a potential position, and analog output may also be used when measuring the sheet width H of a potential position. In this case, it can be determined whether a potential position is the neck 101 or simply due to the affect of noise or the like, by slowing the conveying speed V2 when measuring the sheet width H of a potential position, or shortening the measurement intervals. In this case, there may be an effect from noise or the like when detecting the sheet width H of a potential position.

Therefore, in the weld detecting method of the second example embodiment, analog output is preferably used when measuring the sheet width H when calculating a potential position, and digital output is preferably used when measuring the sheet width H of a potential position.

In this way, the sheet width H of the work is measured using analog output in the process of calculating the potential positions of the neck 101 (i.e., steps S540 to S740). Accordingly, the sheet width H can be measured at a faster conveying speed V2 compared with when the sheet width H of the work is measured using digital output. That is, the time that it takes to calculate potential positions can be reduced.

Also, the sheet width H of the work is measured using digital output in the process of measuring the sheet width H of potential positions at low speed (i.e., steps S570 to S770). Accordingly, the accuracy with which the weld Y is detected can be improved because there is no affect from noise or the like as there is when the sheet width H of the work is measured using analog output.

Also, in the weld detecting method of this example embodiment, the high conveying speed V1 and the low conveying speed V2 are predetermined speeds, but the invention is not limited to this. That is, in the weld detecting method, the high conveying speed V1 and the low conveying speed V2 may also be set by performing a process to set the conveying speed of the work, such as that in the first example embodiment (i.e., steps S150 and S350), before detecting potential positions.

Accordingly, the conveying speed V1 may be set to an optimal speed for the calculation of potential positions. Also, the conveying speed V2 may be set to an optimal speed for the detection of the neck 101. That is, the time that it takes to detect the weld Y on the work can be reduced.

However, from the viewpoint of improving the accuracy with which the weld Y is detected, when no potential positions are able to be detected, it is preferable to perform a process to reset the measurement intervals with the analog output and the high conveying speed V1 (i.e., steps S210 and S420), or set the high conveying speed V1 to a somewhat slower speed. Also, when the weld Y is unable to be detected, it is preferable to perform a process to reset the measurement intervals with the digital output and the low conveying speed V2 (i.e., steps S210 and S420), or set the low conveying speed V2 that is to be set to a somewhat slower speed.

Also, in the weld detecting method of the second example embodiment, the sheet width H is measured with analog output and digital output by a single detecting mechanism 20. However, the invention is not limited to this. That is, in the weld detecting method, the weld Y may be detected using a first detecting mechanism that measures the sheet width H of the work with analog output, and a second detecting mechanism that measures the sheet width H of a potential position with digital output. In this case, the measuring position 20a is a position where the second detecting mechanism that detects the weld Y measures the sheet width. H of the work.

Also, the time that it takes to detect the weld Y on the work can be made even shorter by arranging the first detecting mechanism upstream of the work 100 in the conveying direction, and arranging the second detecting mechanism downstream of the work 100 in the conveying direction. More specifically, the sheet width H is measured by the first detecting mechanism at high speed, and when the potential position is conveyed to the measuring position 20a, the sheet width H of a potential position is measured by the second detecting mechanism at low speed. As a result, the weld Y can be detected with the work being conveyed once, so the time that it takes to detect the weld Y on the work can be made even shorter.

Here, the detection of the weld Y when the detecting mechanism 20 is configured to detect a weld trace formed when the work 100 is welded by image processing will now be described.

When the work 100 is welded, a weld trace is formed continuing along the welded portion in the width direction of the sheet. The width of the weld trace increases by the work 100 being elongated by rolling or the like. Therefore, the width of the weld trace can be calculated by the amount of elongation, the sheet thickness D, and the amount of gradual change C in the sheet width as described above.

Here, the viewability of the weld trace changes depending on the welding conditions. Therefore, the low conveying speed V2 may need to be slowed down depending on the welding conditions. In other words, in the process of setting the low conveying speed V2, it is necessary to take into account the factor that causes the viewability of the weld trace to change.

In this case, information about the factor that causes the viewability to change is necessary when setting the low conveying speed V2. Thus, a process for inputting information about the factor that causes the viewability to change and the like is necessary. That is, the number of processes necessary to detect the weld Y ends up increasing, which in turn increases the amount of time that it takes to detect the weld Y. Also, when measuring works 100 used for different purposes and the like, information about the state and the like during welding of the work 100 is necessary, so the general versatility ends up decreasing.

On one hand, the shape of the neck 101 may change slightly due to the influence of the welding conditions or the like, but in this case, the effect on the detection of the neck 101 is small. That is, when detecting the neck 101, the weld Y can be reliably detected without being affected by the welding conditions or the like.

Also, when detecting the weld Y using an eddy current, the detection accuracy ends up decreasing when heat-treatment is performed in the manufacturing process, as it is with the metal ring of the example embodiment.

If, on the other hand, the weld Y is detected using a laser sensor, as in this example embodiment, the weld Y can be reliably detected without the detection accuracy decreasing due to heat-treatment. In this way, a mechanism that measures the sheet width H of the work is preferably used in a method for detecting the weld Y. However, considering the possibility of damage to the work 100, a mechanism that measures the sheet width H of the work without contacting the work 100, such as a non-contact laser sensor or the like, is preferably used.

Accordingly, the weld Y can be detected without detection being affected by a change in composition due to heat-treatment and the welding conditions.

Incidentally, in the weld detecting method of this example embodiment, the weld Y on a metal ring and metal band are detected, but the invention is not limited to this. That is, the weld detecting method may be broadly applied to a member in which the neck 101 is produced by a welded portion being rolled.

Also, in the weld detecting method of this example embodiment, the work 100 is conveyed for a distance that is sufficiently longer than the length of the work in the longitudinal direction or the circumferential length W of the work, when measuring the sheet width H and detecting the neck 101. However, the invention is not limited to this. That is, in the weld detecting method, the sheet width H of the work simply needs to be able to be measured and the neck 101 simply needs to be able to be detected. For example, the work 100 may also be conveyed for a distance that is sufficiently longer than one-half of the length of the work in the longitudinal direction or the circumferential length W of the work by arranging two detecting mechanisms 20.

Also, the conveying mechanism 10 is configured to convey the work 100, but the invention is not limited to this. That is, the conveying mechanism 10 may also be configured to move the detecting mechanism 20 along the shape of the work 100. In this case, the speed at which the detecting mechanism 20 is moved is the conveying speed V2 when detecting the neck 101. That is, the conveying speed V1 and the conveying speed V2 in this example embodiment are relative speeds of the work 100 with respect to the detecting mechanism 20.

Also, in the weld detecting method of this example embodiment, the measurement intervals are set to the shortest intervals at which the detecting mechanism 20 is capable of taking measurements, but the invention is not limited to this. That is, the measurement intervals may also be set to intervals that are longer than the shortest intervals at which the detecting mechanism 20 is capable of taking measurements. In this case, the number of times that the sheet width H of the work is measured is reduced so the time that it takes to calculate the potential positions and the like can be shortened.

The invention claimed is:

1. A weld detecting method that detects a weld on a work, by detecting a neck formed at the weld on the work, when elongating the work, comprising:
    obtaining at least one correlation, from among a correlation between a width of the neck and an amount of elongation of the work and a correlation between the width of the neck and an amount of change in at least one of a sheet thickness and a sheet width of the work before and after elongation of the work;
    calculating the width of the neck based on the at least one correlation by obtaining at least one of the sheet thickness, the sheet width, and the amount of elongation of the work from the obtained at least one correlation;
    setting a conveying speed of the work when detecting the neck, according to the calculated width of the neck; and
    detecting the neck by measuring the sheet width of the work at predetermined intervals, while conveying the work at the set conveying speed of the work.

2. The weld detecting method according to claim 1, further comprising:
    resetting at least one of the measurement intervals of the sheet width of the work and the conveying speed of the work when detecting the neck, when the neck is not detected, wherein
    detection of the neck is performed by measuring the sheet width of the work at the reset conveying speed and/or the reset measurement intervals.

3. A weld detecting method that detects a weld on a work having a weld, by detecting a neck formed at the weld on the work, while conveying the work at a predetermined conveying speed, when elongating the work, comprising:
    calculating a potential position of the neck by measuring a sheet width of the work, while conveying the work at a speed faster than the predetermined conveying speed; and
    detecting the neck by measuring the sheet width of the work at the calculated potential position, at the predetermined conveying speed.

4. The weld detecting method according to claim 3, wherein the sheet width of the work is measured using analog output when conveying the work at the speed faster than the predetermined conveying speed; and the sheet width of the work at the potential position is measured using digital output when measuring the sheet width of the work at the calculated potential position.

5. A weld detecting apparatus that detects a weld on a work, by detecting a neck formed at the weld on the work, when elongating the work, comprising:
    a conveying mechanism that conveys the work;
    a detecting mechanism that detects an amount of elongation, a sheet width, and a sheet thickness of the work;
    a calculating portion that calculates a width of the neck based on at least one correlation, from among a correlation between the width of the neck and the amount of elongation of the work and a correlation between the width of the neck and an amount of change in at least one of the sheet thickness and the sheet width of the work before and after elongation of the work; and a setting portion that sets a conveying speed of the conveying mechanism according to the calculated width of the neck, wherein the neck is detected by measuring the sheet width of the work at predetermined intervals by the detecting mechanism, while conveying the work at the set conveying speed.

6. A weld detecting apparatus that detects a weld on a work, by detecting a neck formed at the weld on the work while conveying the work at a predetermined conveying speed, when elongating the work, comprising:

a conveying mechanism that conveys the work;

a detecting mechanism that detects an amount of elongation, a sheet width, and a sheet thickness of the work; and a calculating portion that sets a conveying speed of the conveying mechanism to a speed faster than the predetermined conveying speed, and calculates a potential position of the neck by measuring the sheet width of the work by the detecting mechanism while conveying the work, wherein the neck is detected by measuring the sheet width of the work at the calculated potential position, at the predetermined conveying speed.

* * * * *